(12) United States Patent
Miyajiri et al.

(10) Patent No.: US 10,098,655 B2
(45) Date of Patent: Oct. 16, 2018

(54) ULTRASONIC TREATMENT INSTRUMENT

(71) Applicant: OLYMPUS CORPORATION, Hachioji-shi, Tokyo (JP)

(72) Inventors: Satoshi Miyajiri, Tachikawa (JP); Kazuhiro Morisaki, Yokohama (JP); Yuji Hirai, Sagamihara (JP); Takeshi Onaga, Koshigaya (JP); Katsushi Ide, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/489,419

(22) Filed: Apr. 17, 2017

(65) Prior Publication Data

US 2017/0215913 A1    Aug. 3, 2017

Related U.S. Application Data

(63) Continuation of application No. PCT/JP2016/063911, filed on May 10, 2016.

(30) Foreign Application Priority Data

May 12, 2015  (JP) ................................. 2015-097403

(51) Int. Cl.
*A61B 17/32* (2006.01)
*A61N 7/00* (2006.01)
*A61B 17/00* (2006.01)
*A61B 18/00* (2006.01)

(52) U.S. Cl.
CPC ........ *A61B 17/320092* (2013.01); *A61N 7/00* (2013.01); *A61B 2017/00393* (2013.01);
(Continued)

(58) Field of Classification Search
CPC .. A61B 17/320092; A61B 2018/00589; A61B 2018/00607
See application file for complete search history.

(56) References Cited

U.S. PATENT DOCUMENTS 5,906,628 A      5/1999   Miyawaki et al.
2002/0198555 A1  12/2002  White et al.
(Continued)

FOREIGN PATENT DOCUMENTS

JP   H10-05237 A    1/1998
JP   2001-070313 A  3/2001
(Continued)

OTHER PUBLICATIONS

Jul. 26, 2016 Search Report issued in International Patent Application No. PCT/JP2016/063911.
(Continued)

*Primary Examiner* — Kathleen Holwerda
*Assistant Examiner* — Sarah Simpson
(74) *Attorney, Agent, or Firm* — Oliff PLC

(57) ABSTRACT

An ultrasonic treatment instrument includes a vibration transmitting member transmitting ultrasonic vibration toward a first gripper and formed as one piece, and a second gripper movable between a spaced position where the second gripper is spaced apart from the first gripper and a closed position where the second gripper is put in close to the first gripper. The ultrasonic treatment instrument includes an interlocking actuator increasing, by moving the first gripper in interlock with a movement of the second gripper to the spaced position, a spacing distance between the first gripper and the second gripper in accordance with a movement of the first gripper.

5 Claims, 11 Drawing Sheets

(52) U.S. Cl.
CPC ............... *A61B 2018/00589* (2013.01); *A61B 2018/00607* (2013.01)

(56) References Cited

U.S. PATENT DOCUMENTS

| | | | |
|---|---|---|---|
| 2004/0199194 A1* | 10/2004 | Witt ............... | A61B 17/320092 606/169 |
| 2010/0331873 A1 | 12/2010 | Dannaher et al. | |
| 2012/0101495 A1* | 4/2012 | Young ................... | A61B 17/29 606/41 |
| 2013/0110155 A1 | 5/2013 | Tsuchiya et al. | |
| 2014/0005702 A1 | 1/2014 | Timm et al. | |
| 2015/0164531 A1* | 6/2015 | Faller ............. | A61B 17/320092 606/169 |

FOREIGN PATENT DOCUMENTS

| | | |
|---|---|---|
| JP | 2005-525180 A | 8/2005 |
| JP | 2012-531970 A | 12/2012 |
| JP | 2015-521901 A | 8/2015 |
| WO | 2003/0095028 A1 | 11/2003 |
| WO | 2012/128362 A1 | 9/2012 |
| WO | 2014/004112 A1 | 1/2014 |

OTHER PUBLICATIONS

Nov. 23, 2017 International Preliminary Report on Patentability issued in International Patent Application No. PCT/JP2016/063911.

* cited by examiner

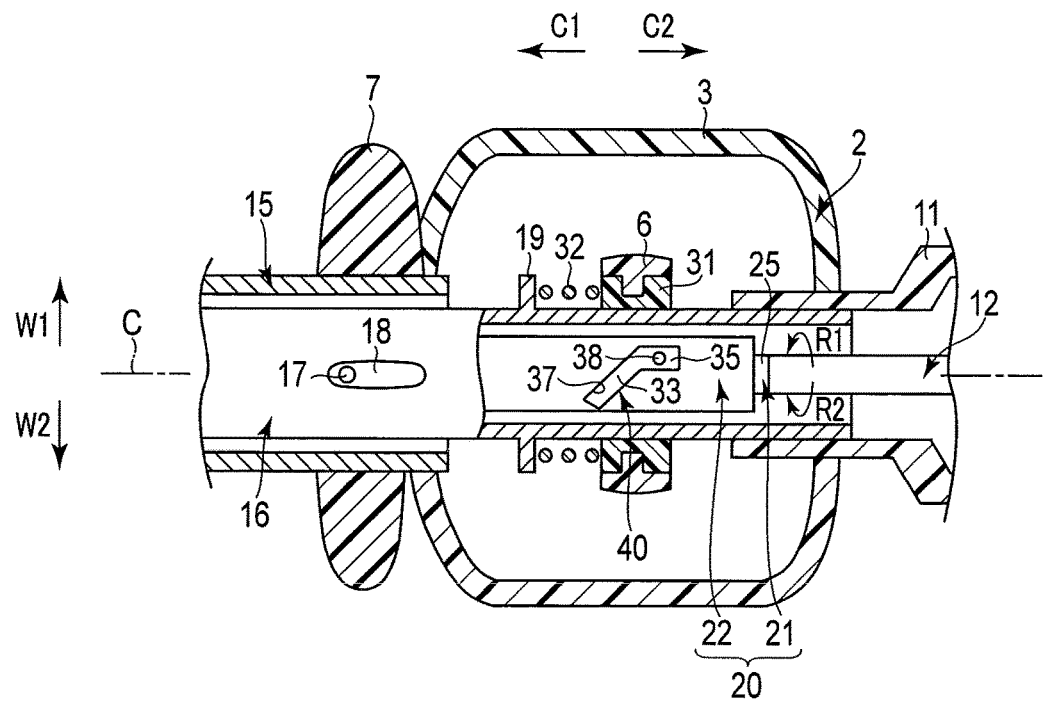
F I G. 3
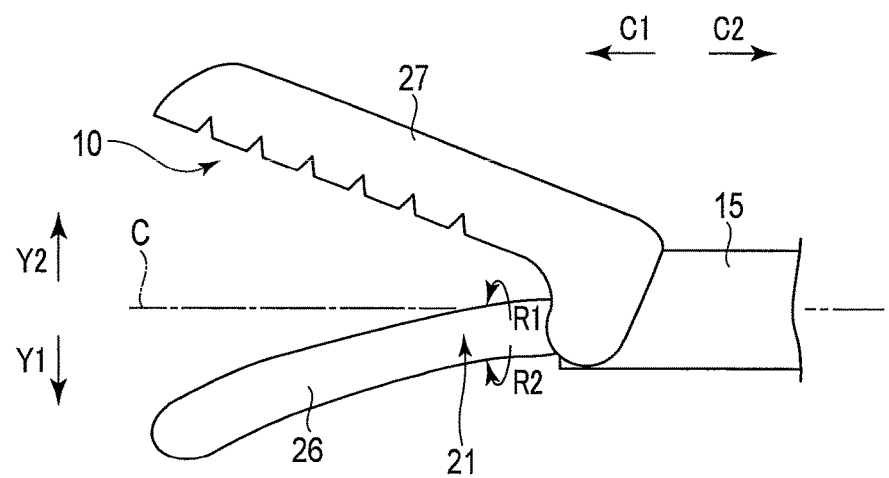
F I G. 4

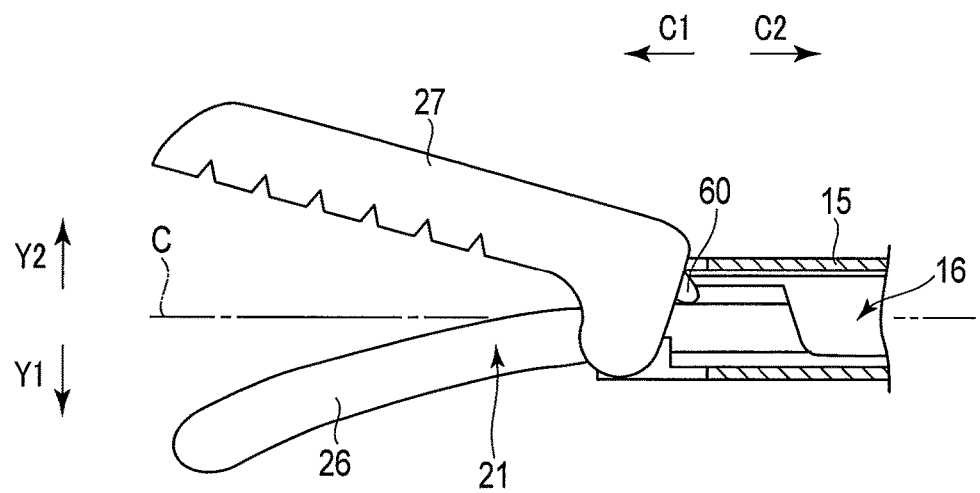
F I G. 19
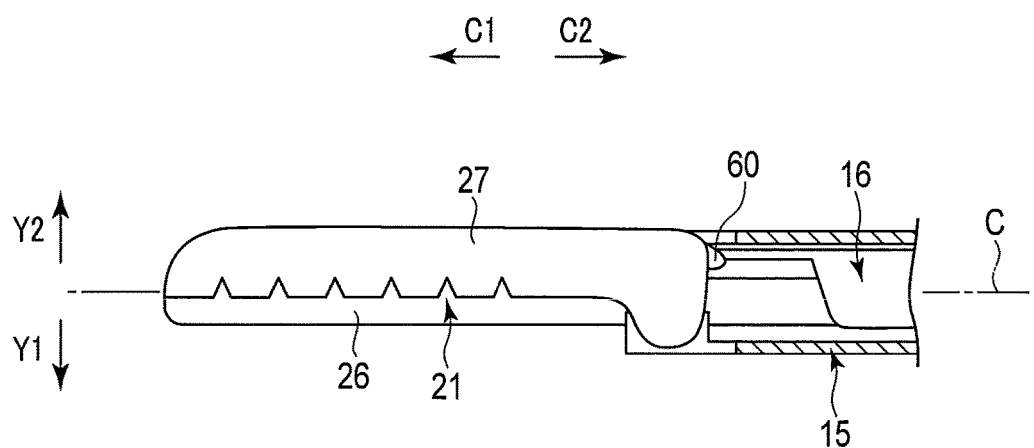
F I G. 20

ULTRASONIC TREATMENT INSTRUMENT

CROSS-REFERENCE TO RELATED APPLICATIONS

This is a Continuation Application of PCT Application No. PCT/JP2016/063911, filed May 10, 2016 and based upon and claiming the benefit of priority from prior Japanese Patent Application No. 2015-097403, filed May 12, 2015, the entire contents of which are incorporated herein by reference.

BACKGROUND OF THE INVENTION

1. Field of the Invention

The present invention relates to an ultrasonic treatment instrument which treats, by using ultrasonic vibration, a treated target that is grasped between a first gripper and a second gripper.

2. Description of the Related Art

PCT International Publication 2003/095028 discloses an ultrasonic treatment instrument in which a first gripper (blade) and a second gripper (clamp) are rotatably attached to a distal portion of a vibration transmitting member (ultrasonic transmission coupler) which extends along a longitudinal axis. In this ultrasonic treatment instrument, when the first gripper and second gripper are opened with respect to each other, the first gripper is rotated in a direction away from the second gripper, and the second gripper is rotated in a direction away from the first gripper. In addition, the vibration transmitting member transmits ultrasonic vibration toward a distal side. Furthermore, ultrasonic vibration is transmitted from the vibration transmitting member to at least one of the first gripper and the second gripper via a rotational center of the first gripper and second gripper (an attachment position of the first gripper and second gripper to the vibration transmitting member). An end effector, which is formed of the first gripper and second gripper, treats a treated target, which is grasped between the first gripper and second gripper, by using the transmitted ultrasonic vibration. Besides, a treated target is peeled off by opening the first gripper and second gripper with respect to each other from the closed state.

BRIEF SUMMARY OF THE INVENTION

According to one aspect of the invention, an ultrasonic treatment instrument including: a vibration transmitting member having a longitudinal axis, including a first gripper in a distal portion thereof, and configured to transmit ultrasonic vibration toward the first gripper, the vibration transmitting member being formed as one piece; a second gripper which is movable between a spaced position where the second gripper is spaced apart from the first gripper and a closed position where the second gripper is put in close to the first gripper; and an interlocking actuator configured to increase, by moving the first gripper in interlock with a movement of the second gripper to the spaced position, a spacing distance between the first gripper and the second gripper in accordance with a movement of the first gripper.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a cross-sectional view which schematically illustrates the internal configuration of the housing according to the first embodiment by a cross section which is parallel to a longitudinal axis and is parallel to the width direction of the housing, FIG. 4 is a schematic view illustrating a configuration of a first gripper and a second gripper according to the first embodiment, in a state in which the second gripper is located in a spaced position, FIG. 19 is a schematic view illustrating the configuration of the first gripper and second gripper according to the sixth embodiment, in a state in which the second gripper is located in the spaced position, and FIG. 20 is a schematic view illustrating the configuration of the first gripper and second gripper according to the sixth embodiment, in a state in which the second gripper is located in the closed position.

DETAILED DESCRIPTION OF THE INVENTION

First Embodiment

A first embodiment of the present invention will be described with reference to FIG. 1 to FIG. 5.

Figure 1:
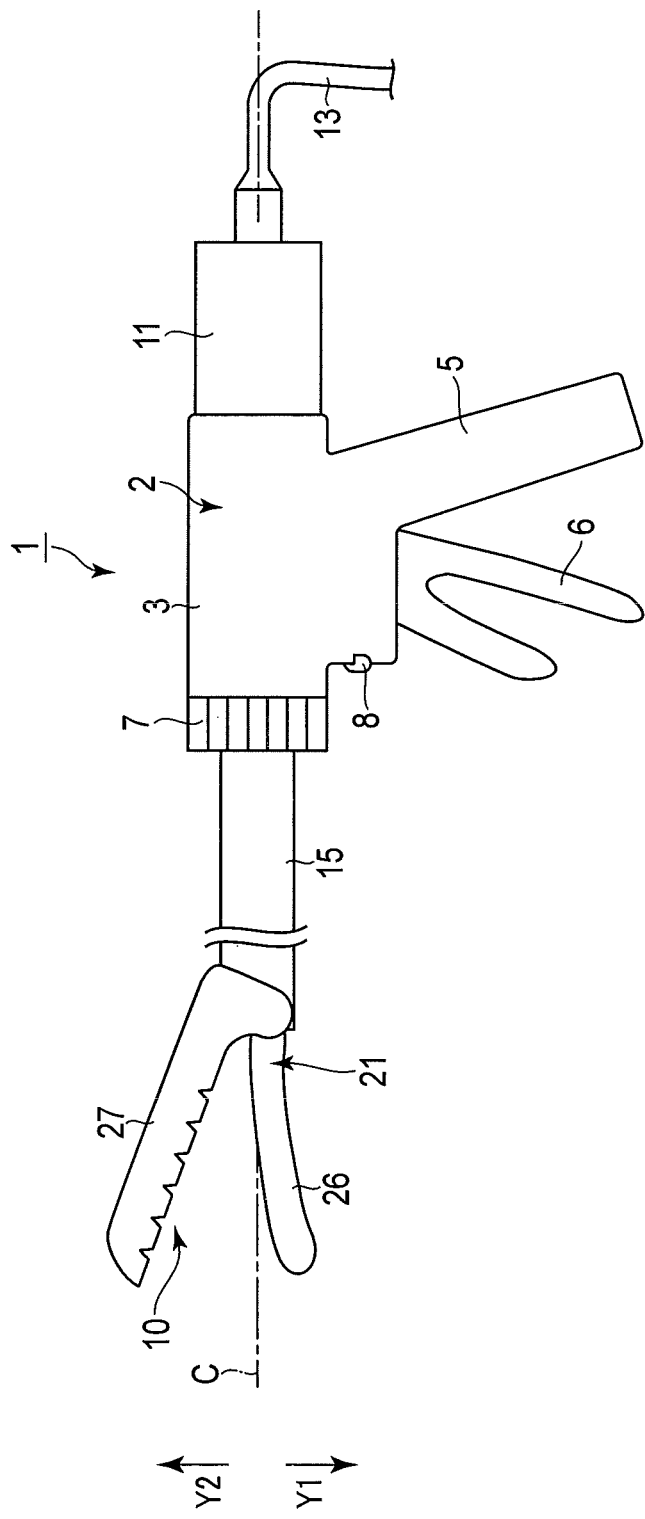
FIG. 1 is a schematic view illustrating an ultrasonic treatment instrument according to a first embodiment.

FIG. 1 is a view illustrating an ultrasonic treatment instrument 1 according to the first embodiment. As illustrated in FIG. 1, the ultrasonic treatment instrument 1 has a longitudinal axis C. Here, one side of a direction along the longitudinal axis C is a distal side (an arrow C1 side in FIG. 1), and the side opposite to the distal side is a proximal side (an arrow C2 side in FIG. 1). The ultrasonic treatment instrument 1 includes a housing 2 which can be held. The housing 2 includes a housing main body 3 which extends along the longitudinal axis C, and a grip (stationary handle) 5 which extends from the housing main body 3 in a direction crossing the longitudinal axis C. In addition, a handle (movable handle) 5 is rotatably attached to the housing 2. By the handle 6 rotating relative to the housing 2, the handle 6 opens or closes relative to the grip 5.

Figure 2:
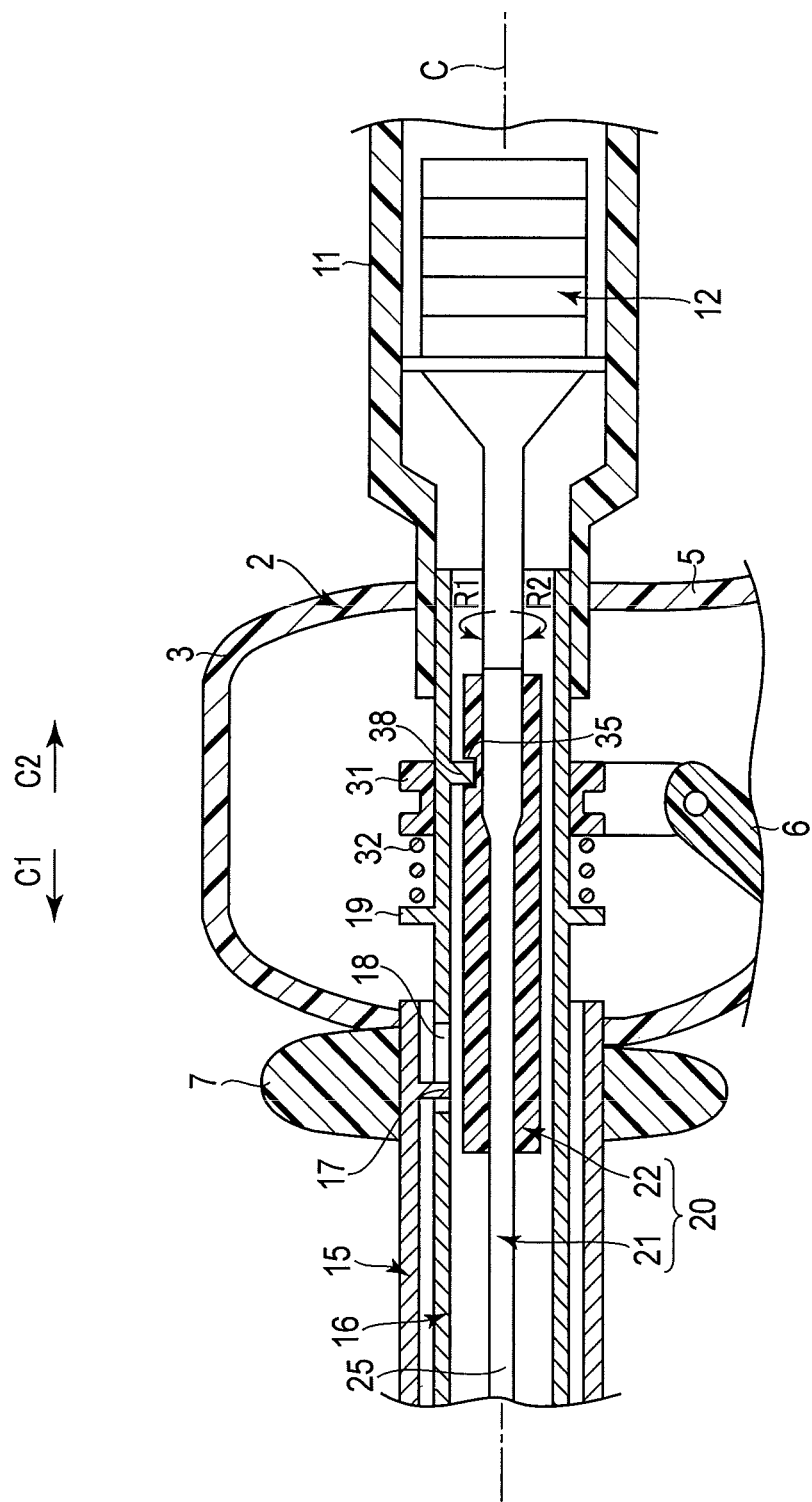
FIG. 2 is a cross-sectional view which schematically illustrates an internal configuration of a housing according to the first embodiment by a cross section perpendicular to a width direction of the housing.

FIG. 2 and FIG. 3 are views illustrating an internal configuration of the housing 2. FIG. 2 shows a cross section perpendicular (substantially perpendicular) to a width direction (a direction indicated by an arrow W1 and an arrow W2 in FIG. 3) of the housing 2. FIG. 3 shows a cross section which is parallel (substantially parallel) to the longitudinal axis C and is parallel (substantially parallel) to the width direction of the housing 2. As illustrated in FIG. 1 to FIG. 3, a transducer case 11 is coupled to the housing 2 in a state in which the transducer case 11 is inserted into an inside of the housing main body 3 from the proximal side. A vibration generator (ultrasonic transducer) 12, which generates ultrasonic vibration, is provided in the transducer case 11. In addition, one end of a cable 13 is connected to the transducer case 11. The other end of the cable 13 is detachably connected to an energy source (not shown). By electric energy (AC current) being supplied from the energy source via an electric wiring line (not shown) which extends in the inside of the cable 13, the electric energy is converted to ultrasonic vibration by a piezoelectric element provided in the vibration generator 12, and the ultrasonic vibration is generated.

An operation button 8, which is pushed by an operation input, is attached to the housing 2. A switch (not shown) is provided in the inside of the housing 2, and the opening or closing of the switched is changed over, based on the operation input by the operation button 8. The switch is connected to the energy source via a signal path (not shown) which extends though the inside of the housing case 2, the transducer case 11 and the inside of the cable 13. By detecting the opening or closing of the switch, the energy source detects whether the operation input is being executed by the operation button 8. If the operation input by the operation button 8 was detected, the energy source supplies electric energy to the vibration generator 12.

A rotary knob 7 is coupled to the distal side of the housing main body 3 such that the rotary knob 7 is rotatable about the longitudinal axis C. In addition, a cylindrical sheath 15 is coupled to the housing 2 in a state in which the sheath 15 is inserted into the inside of the rotary knob 7 and the inside of the housing body 3 from the distal side. The sheath 15 extends along the longitudinal axis C, and is fixed to the rotary knob 7. Thus, by rotating the rotary knob 7 relative to the housing 2, the sheath 15 rotates around the longitudinal axis C together with the rotary knob 7 relative to the housing 2. Specifically, the sheath 15 is rotatable about the longitudinal axis. C relative to the housing 2.

In the ultrasonic treatment instrument 1, a cylindrical movable shaft 16 extends toward the distal side from the inside of the housing main body 3 through the inside of the sheath 15. Specifically, the sheath 15 covers the movable shaft 16 from an outer peripheral side (a direction away from the longitudinal axis C). A projection 17, which projects toward an inner peripheral side (a direction toward the longitudinal axis C), is formed in the sheath 15, and an engaging hole 18, with which the projection 17 is engageable, is formed in the movable shaft 16 in a slit shape along the longitudinal axis C. The projection 17 is movable in the engaging hole 18 along the longitudinal axis C, but the movement of the projection 17 around the longitudinal axis C is restricted by an edge of the engaging hole 18. Thus, although the movable shaft 16 is movable along the longitudinal axis C relative to the sheath 15 and housing 2, the rotation of the movable shaft 16 around the longitudinal axis C relative to the sheath 15 is restricted. Accordingly, by the rotary knob 7 and sheath 15 rotating, the movable shaft 16 rotates around the longitudinal axis C together with the rotary knob 7 and sheath 15.

In addition, in the ultrasonic treatment instrument 1, an extension unit 20 extends toward the distal side from the inside of the housing main body 3 through the inside of the movable shaft 16 (the inside of the sheath 15). The extension unit 20 includes a vibration transmitting member (probe) 21 which can transmit ultrasonic vibration, and a cylindrical holding member 22 which covers the vibration transmitting member 21 from the outer peripheral side. The movable shaft 16 covers the extension unit 20 (vibration transmitting member 21 and cylindrical holding member 22) from the outer peripheral side, and the holding member 22 is disposed between the vibration transmitting member 21 and movable shaft 16 in the radial direction. The vibration transmitting member 21 is formed of a material with a high vibration transmissibility, such as a titanium alloy or duralumin, and the holding member 22 is formed of a material with a low vibration transmissibility, such as a resin. Thus, the holding member 22 has a lower vibration transmissibility than the vibration transmitting member 21.

The holding member 22 is fixed to the vibration transmitting member 21, and holds the vibration transmitting member 21. In addition, the holding member 22 extends over only a range from the inside of the housing main body 3 to the inside of the rotary knob 7, and a distal end of the holding member 22 is located on the proximal side with respect to a distal end of the sheath 15 (a distal end of the movable shaft 16). Accordingly, the vibration transmitting member 21 is inserted through the holding member 22.

The vibration transmitting member 21 includes a transmitting member main body 25, and a first gripper (probe treatment portion) 26 which is provided on the distal side with respect to the transmitting member main body 25. Since the vibration transmitting member 21 is a single member, the transmitting member main body 25 and first gripper 26 are formed as one piece. The vibration transmitting member 21 is inserted through the sheath 15 (movable shaft 16), and the first gripper 26 projects toward the distal side from the distal end of the sheath 15 (distal end of the movable shaft 16). The transmitting member main body 25 extends substantially straight with its axial center agreeing with the longitudinal axis C. Specifically, the vibration transmitting member 21 has the longitudinal axis C that is the axial center of the transmitting member main body 25. The first gripper 26 is curved relative to the longitudinal axis C (transmitting member main body 25).

In the inside of the housing main body 3, the vibration generator 12 is connected to the vibration transmitting member 21 from the proximal side. Ultrasonic vibration, which is generated by the vibration generator 12, is transmitted to the vibration transmitting member 21, and the ultrasonic vibration is transmitted toward the first gripper 26 in the vibration transmitting member 21 from the proximal side to the distal side. By transmitting the ultrasonic vibration generated by the vibration generator 12, the vibration transmitting member 21 vibrates (longitudinally vibrates) in a predetermined frequency range (e.g. 46 kHz to 48 kHz) with a vibration direction being a direction along the longitudinal axis C. At this time, since the vibration transmissibility of the holding member 22 is low, the holding member 22 hardly vibrates even if the ultrasonic vibration is transmitted from the vibration transmitting member 21 to the holding member 22.

A second gripper (jaw) 27 is rotatably attached to the distal portion of the sheath 15. By the second gripper 27 rotating about the attachment position to the sheath 15, the second gripper 27 moves relative to the first gripper 26 between a spaced position where the second gripper 27 is spaced apart from the first gripper 26 and a closed position where the second gripper 27 is put in close to the first gripper 26. The direction of movement (opening or closing direction) of the second gripper 27 between the spaced position and closed position crosses (is substantially perpendicular to) the longitudinal axis C, and crosses (is substantially perpendicular to) the width direction of the housing 2 (the width direction of the second gripper 27). By the sheath 15 rotating around the longitudinal axis C, the second gripper 27 also rotates together with the sheath 15. In the present embodiment, an end effector, which treats a treated target, is formed by the first gripper 26 and second gripper 27. In the meantime, in the state in which the second gripper 27 is located in the closed position, the second gripper 27 is curved relative to the longitudinal axis C in the same direction as the first gripper 26 is curved relative to the longitudinal axis C. Thus, in the state in which the second gripper 27 is located in the closed position, at least a part of the second gripper 27 can be put in contact with the first gripper 26.

A cylindrical slider member 31 is attached to an outer peripheral surface of the movable shaft 16. The handle 6 is coupled to the slider member 31 in the inside of the housing main body 3. In addition, a cylindrical elastic member 32 extends on the outer peripheral surface of the movable shaft 16. A proximal end (one end) of the elastic member 32 is connected to the slider member 31, and a distal end (the other end) of the elastic member 32 is connected to a receiving portion 19 of the movable shaft 16. The slider member 31 and elastic member 32 are rotatable together with the movable shaft 16 (rotary knob 7) around the longitudinal axis C relative to the handle 6. In addition, in this embodiment, the slider member 31 and elastic member 32 are located on the proximal side with respect to a proximal end of the sheath 15, and are located on the proximal side with respect to the engaging hole 18.

By opening or closing the handle 6 relative to the grip 5, a moving force from the handle 6 is transmitted to the movable shaft 16 through the slider member 31 and elastic member 32, and the movable shaft 16 moves along the longitudinal axis C relative to the sheath 15 and extension unit 20 (vibration transmitting member 21 and holding member 22). A distal end of the movable shaft 16 is connected to the second gripper 27. By the movable shaft 16 moving along the longitudinal axis C, the second gripper 27 moves (rotates) between the spaced position and the closed position. Here, in this embodiment, the handle 6 is closed relative to the grip 5 and the movable shaft 16 moves toward the distal side, and thereby the second gripper 27 moves toward the closed position. On the other hand, the handle 6 is opened relative to the grip 5 and the movable shaft 16 moves toward the proximal side, and thereby the second gripper 27 moves toward the spaced position.

In addition, in an outer peripheral surface of the holding member 22, a first guide groove 33 and a second guide groove 35, which are recessed toward the inner peripheral side, are formed by a groove forming surface (groove forming portion) 37. The first guide groove 33 extends from one side (an arrow R1 side in each of FIG. 2 and FIG. 3) toward the other side (an arrow R2 side in each of FIG. 2 and FIG. 3) around the longitudinal axis C as extending from the proximal side toward the distal side. Specifically, the first guide groove 33 extends in an inclined state relative to the longitudinal axis C. The first guide groove 33 extends over an angle range of at least 90° around the longitudinal axis C. The second guide groove 35 extends along the longitudinal axis C (in a non-inclined state relative to the longitudinal axis C), and is continuous with a proximal end (one end) of the first guide groove 33.

On an inner peripheral surface of the movable shaft 16, an engaging projection (engaging portion) 38, which projects toward the inner peripheral side, is formed. In the present embodiment, the engaging projection 38 is located on the proximal side with respect to the engaging hole 18. The engaging projection 38 is provided in the movable shaft 16 at such a position that the engaging projection 38 is engageable with the first guide groove 33 and second guide groove 35, and the engaging projection 38 is movable in the first guide groove 33 and second guide groove 35. By opening or closing the handle 6 relative to the grip 5, the movable shaft 16 moves along the longitudinal axis C, and thereby the engaging projection 38 moves along the first guide groove 33 and second guide groove 35. Specifically, in accordance with the movement of the movable shaft 16 along the longitudinal axis C, the position of the engaging projection 38 varies in the first guide groove 33 and second guide groove 35. In the meantime, since the vibration transmissibility of the holding member 22 is low, ultrasonic vibration is not transmitted from the vibration transmitting member 21 to the movable shaft 16 and sheath 15 through the holding member 22 and engaging projection 38.

In the state in which the second gripper 27 is located in the spaced position relative to the first gripper 26, the engaging projection 38 is located in the second guide groove 35. Although the engaging projection 38 is movable along the longitudinal axis C (the second guide groove 35) in the second guide groove 35, the movement of the engaging projection 38 around the longitudinal axis C is restricted by the edge of the second guide groove 35. Thus, in the state in which the engaging projection 38 is located in the second guide groove 35, the movable shaft 16 is movable along the longitudinal axis C relative to the extension unit 20, but the movement of the movable shaft 16 around the longitudinal axis C relative to the extension unit 20 is restricted. Accordingly, in the state in which the engaging projection 38 is located in the second guide groove 35, by the movable shaft 16 rotating around the longitudinal axis C together with the rotary knob 7 and sheath 15, a rotational driving force is transmitted from the movable shaft 16 to the holding member 22 through the engaging projection 38 in the second guide groove 35, and the extension unit 20 (vibration transmitting member 21 and holding member 22) rotates together with the movable shaft 16 around the longitudinal axis C. Accordingly, in the state in which the second gripper 27 is located in the spaced position relative to the first gripper 26 (the state in which the engaging projection 38 is located in the second guide groove 35), the sheath 15, movable shaft 16, extension unit 20 and second gripper 27 rotate together around the longitudinal axis C by rotating the rotary knob 7.

By closing the handle 6 relative to the grip 5 from the state in which the second gripper 27 is located in the spaced position, the movable shaft 16 moves to the distal side relative to the sheath 15 and extension unit 20, and the second gripper 27 rotates toward the closed position. At this time, in accordance with the movement of the movable shaft 16 to the distal side, the engaging projection 38 moves from the second guide groove 35 to the first guide groove 33, and moves in the first guide groove 33 from the proximal side to the distal side. By the engaging projection 38 moving to the distal side in the first guide groove 33, pushing force acts on the extension unit 20 from the engaging projection 38, and the pushing force is decomposed into a component element to the distal side and a component element to one side around the longitudinal axis C (the arrow R1 side in each of FIG. 2 and FIG. 3). By the component element of the pushing force from the engaging projection 38 to the one side around the longitudinal axis C (first periaxial direction), the extension unit 20 rotates to the one side around the longitudinal axis C (first periaxial direction) relative to the sheath 15 and movable shaft 16. Thereby, the first gripper 26 rotates toward the one side around the rotational axis C (in a predetermined direction) relative to the second gripper 27.

In addition, in the state in which the second gripper 27 is located in the closed position, the engaging projection (engaging portion) 38 is located in the first guide groove 33. By opening the handle 6 relative to the grip 5 from this state, the movable shaft 16 moves to the proximal side relative to the sheath 15 and extension unit 20, and the second gripper 27 rotates toward the spaced position. At this time, in accordance with the movement of the movable shaft 16 to the proximal side, the engaging projection 38 moves from the distal side to the proximal side in the first guide groove 33 toward the second guide groove 35. By the engaging projection 38 moving to the proximal side in the first guide groove 33, pushing force acts on the extension unit 20 from the engaging projection 38, and the pushing force is decomposed into a component element to the proximal side and a component element to the other side (the arrow R2 side in each of FIG. 2 and FIG. 3) around the longitudinal axis C. By the component element of the pushing force from the engaging projection 38 to the other side around the longitudinal axis C (second periaxial direction), the extension unit 20 rotates to the other side around the longitudinal axis C (second periaxial direction) relative to the sheath 15 and movable shaft 16. Thereby, the first gripper 26 rotates toward the other side around the rotational axis C (in a predetermined direction) relative to the second gripper 27.

As described above, in the present embodiment, the position of the engaging projection (engaging portion) 38 in the first guide groove 33 varies in accordance with the movement of the movable shaft 16 along the longitudinal axis C. Thus, a linear movement of the movable shaft 16 is converted to a rotational movement of the extension unit 20 (vibration transmitting member 21 and holding member 22) around the longitudinal axis C relative to the movable shaft 16. By the rotational movement of the extension unit 20 relative to the movable shaft 16, the first gripper 26 rotates about the longitudinal axis C relative to the second gripper 27. Accordingly, in the present embodiment, an interlocking actuator 40 is formed by the groove forming surface (groove forming portion) 37 and engaging projection (engaging portion) 38. The interlocking actuator 40 rotates the vibration transmitting member 21, which includes the first gripper 26, about the longitudinal axis C relative to the second gripper 27, in interlock with the movement of the movable shaft 16 along the longitudinal axis C (i.e. the movement of the second gripper 27 between the closed position and the spaced position). Specifically, by the interlocking actuator 40, the first gripper 26 moves (rotates) in interlock with the movement of the second gripper 27 between the closed positon and the spaced position.

Figure 5:
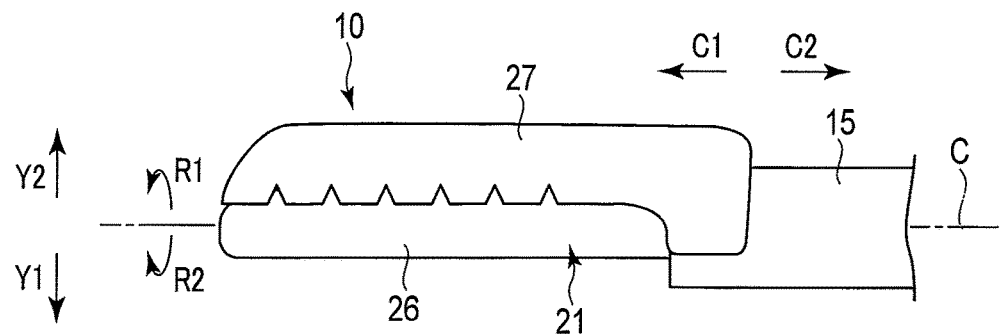
FIG. 5 is a schematic view illustrating a configuration of the first gripper and second gripper according to the first embodiment, in a state in which the second gripper is located in a closed position.

FIG. 4 and FIG. 5 are views illustrating a configuration of the first gripper 26 and second gripper 27. FIG. 4 illustrates a state in which the second gripper 27 is located in the spaced position, and FIG. 5 illustrates a state in which the second gripper 27 is located in the closed position. In addition, FIG. 4 and FIG. 5 illustrate states as viewed from one side in the width direction of the second gripper 27. As illustrated in FIG. 4, in the state in which the second gripper 27 is located in the spaced position relative to the first gripper 26, the first gripper 26 is curved relative to the longitudinal axis C (transmitting member main body 21) toward a side away from the second gripper 27 (an arrow Y1 side in each of FIG. 4 and FIG. 5). If the movable shaft 16 is moved to the distal side, the first gripper 26 rotates by a proper angle relative to the second gripper 27 to the one side around the longitudinal axis C (the arrow R1 side in each of FIG. 4 and FIG. 5), as described above, in interlock with the movement of the second gripper 27 from the spaced position to the closed position. In the present embodiment, the first gripper 26 rotates by about 90° to the one side around the longitudinal axis C (first periaxial direction) in interlock with the movement of the second gripper 27 to the closed position. Incidentally, in each of FIG. 4 and FIG. 5, an arrow Y2 side is a side on which the first gripper 26 approaches the second gripper 27.

In the state in which the second gripper 27 has moved to the closed position by the first gripper 26 rotating by the proper angle relative to the second gripper 27 to the one side around the longitudinal axis C, the first gripper 26 is curved relative to the longitudinal axis C (transmitting member main body 21) toward one side in the width direction of the second gripper 27 (a direction perpendicular to the drawing sheet of each of FIG. 4 and FIG. 5). Thus, the spacing distance between the first gripper 26 and second gripper 27 decreases in accordance with the rotational movement of the first gripper 26 relative to the second gripper 27 toward the one side around the longitudinal axis C, the rotational movement being in interlock with the movement of the second gripper 27 toward the closed position. Accordingly, in the present embodiment, when the first gripper 26 and second gripper 27 are closed with respect to each other by the movement of the movable shaft 16 to the distal side, the spacing distance between the first gripper 26 and second griper 27 decreases due to the movement of the second gripper 27 toward the closed position, and also the spacing distance between the first gripper 26 and second griper 27 decreases due to the rotational movement of the first gripper 26 relative to the second gripper 27 toward the one side around the longitudinal axis C.

On the other hand, if the movable shaft 16 moves to the proximal side, the first gripper 26 rotates relative to the second gripper 27 to the other side around the longitudinal axis C (the arrow R2 side in each of FIG. 4 and FIG. 5) as described above, in interlock with the movement of the second gripper 27 from the closed position to the spaced position. In the present embodiment, the first gripper 26 rotates by about 90° to the other side around the longitudinal axis C (second periaxial direction) in interlock with the movement of the second gripper 27 to the spaced position. Thereby, the first gripper 26 changes from the state in which the first gripper 26 is curved relative to the longitudinal axis C toward the one side in the width direction of the second gripper 27, to the state in which the first gripper 26 is curved relative to the longitudinal axis C toward the side away from the second gripper 27.

As described above, the spacing distance between the first gripper 26 and second gripper 27 increases in accordance with the rotational movement of the first gripper 26 relative to the second gripper 27 toward the other side around the longitudinal axis C, the rotational movement being in interlock with the movement of the second gripper 27 toward the spaced position. Specifically, the spacing distance between the first gripper 26 and second gripper 27 increases in accordance with the movement of the first gripper 26, which is in interlock with the movement of the second gripper 27 toward the spaced position. Accordingly, in the present embodiment, when the first gripper 26 and second gripper 27 are opened with respect to each other by the movement of the movable shaft 16 to the proximal side, the spacing distance between the first gripper 26 and second griper 27 increases due to the movement of the second gripper 27 toward the spaced position, and also the spacing distance between the first gripper 26 and second griper 27 increases due to the rotational movement of the first gripper 26 relative to the second gripper 27 toward the other side around the longitudinal axis C.

Next, the function and advantageous effects of the ultrasonic treatment instrument 1 of the present embodiment will be described. When a treatment is performed by using the ultrasonic treatment instrument 1, the sheath 15, movable shaft 16 and end effector 10 are inserted in a body cavity such as a peritoneal cavity. Then, in the state in which the second gripper 27 is located in the spaced position (the state in which the first gripper 26 and second gripper 27 are opened with respect to each other), a treated target, such as a blood vessel, is disposed between the first gripper 26 and second gripper 27. In addition, by closing the handle 6 relative to the grip 5, the movable shaft 16 is moved to the distal side, and the first gripper 26 and second gripper 27 are closed with respect to each other as described above. Thereby, the treated target is grasped between the first gripper 26 and second gripper 27.

In the present embodiment, the first gripper 26 rotates relative to the second gripper 27 to one side around the longitudinal axis C in interlock with the movement of the second gripper 27 to the spaced position, and the spacing distance between the first gripper 26 and second gripper 27 increases in accordance with the rotational movement (motion) of the first gripper 26 in addition to the movement of the second gripper 27 toward the spaced position. Specifically, when the first gripper 26 and second gripper 27 are opened with respect to each other, both the first gripper 26 and second gripper 27 move to increase the spacing distance between their mutual grasping surfaces. Thus, in the state in which the second gripper 27 is located in the spaced position, the spacing distance between the first gripper 26 and second gripper 27 is large, and it becomes easier to dispose the treated target between the first gripper 26 and second gripper 27. Thereby, the treated target can easily be grasped.

In addition, in the state in which the second gripper 27 is located in the spaced position, the engaging projection 38 is located in the second guide groove 35. Thus, by rotating the rotary knob 7, the sheath 15, movable shaft 16, extension unit 20 and second gripper 27 rotate together around the longitudinal axis C. Hence, in the state in which the second gripper 27 is located in the spaced position, the second gripper 27 can be adjusted at a proper angular position around the longitudinal axis C and the treated target can be grasped.

Besides, by performing an operation input by the operation button 8 in the state in which the treated target is grasped between the first gripper 26 and second gripper 27, the ultrasonic vibration, which is generated by the vibration generator 12, is transmitted to the first gripper 26 through the vibration transmitting member 21, as described above. The end effector 10 treats (e.g. coagulates and, at the same time, cuts and opens) the grasped treated target by using the ultrasonic vibration which has been transmitted to the first gripper 26. In the present embodiment, since the vibration transmitting member 21 (transmitting member main body 25 and first gripper 26) is formed as one piece, the ultrasonic vibration, which has been transmitted from the vibration generator 12 to the vibration transmitting member 21, is properly transmitted to the first gripper 26 of the end effector 10. Accordingly, in the end effector 10, the treatment is properly performed by using the ultrasonic vibration transmitted to the first gripper 26, and the treatment performance of the treated target with use of the ultrasonic vibration can be secured.

Furthermore, a treatment of peeling off a treated target, such as a thin membranous tissue, is also performed by using the ultrasonic treatment instrument 1 of the present embodiment. At this time, in the state in which the second gripper 27 is located in the closed position, the end effector 10 is put in contact with the treated target. Then, by opening the handle 6 relative to the grip 5, the movable shaft 16 moves to the proximal side, and the first gripper 26 and second gripper 27 are opened as described above. Thereby, the treated target is peeled off.

In the present embodiment, when the first gripper 26 and second gripper 27 are opened with respect to each other, both the first gripper 26 and second gripper 27 move to increase the spacing distance from each other. Thus, when the first gripper 26 and second gripper 27 are opened with respect to each other, the opening angle between the first gripper 26 and second gripper 27 from the state in which the second gripper is in the closed position becomes large. Since the opening angle between the first gripper 26 and second gripper 27 becomes large, the amount of peeling of the treated target increases, and the treated target can be easily peeled off.

As described above, in the present embodiment, there can be provided the ultrasonic treatment instrument 1 in which the spacing distance in the state in which the first gripper 26 and second gripper 27 are opened is sufficiently secured and the ultrasonic vibration is properly transmitted to the end effector 10.

Modification of the First Embodiment

Figure 6:
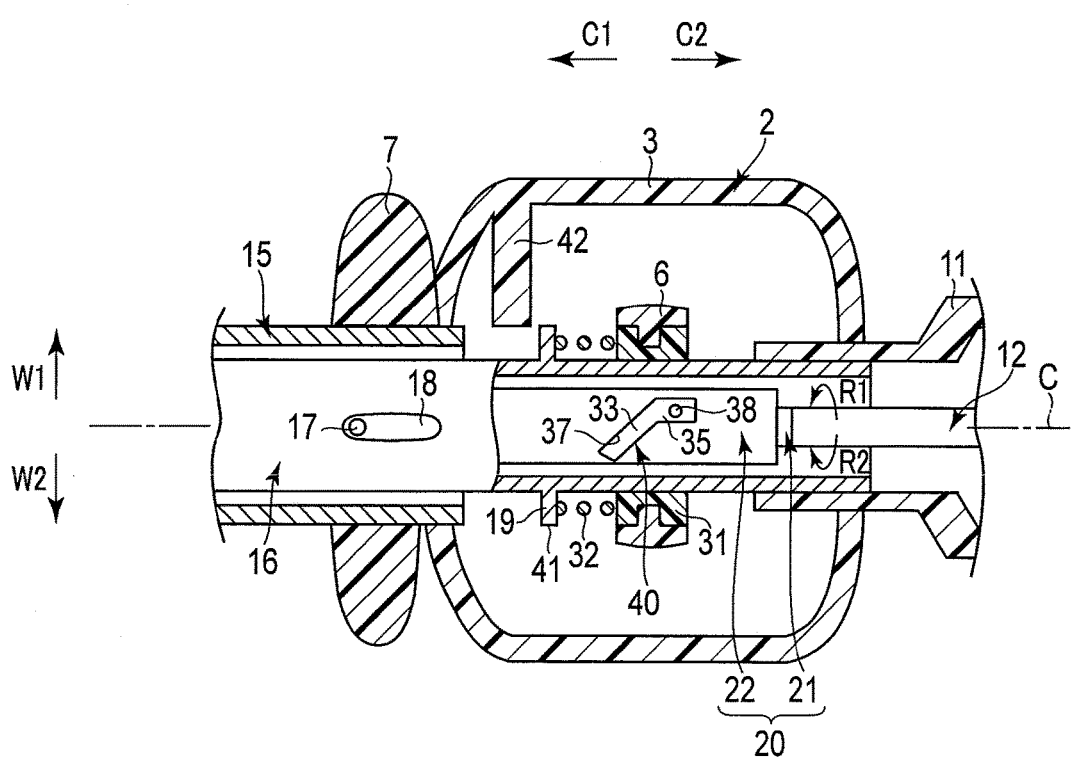
FIG. 6 is a cross-sectional view which schematically illustrates an internal configuration of a housing according to one modification of the first embodiment, in a state in which an engaging projection is located in a second guide groove.
Figure 7:
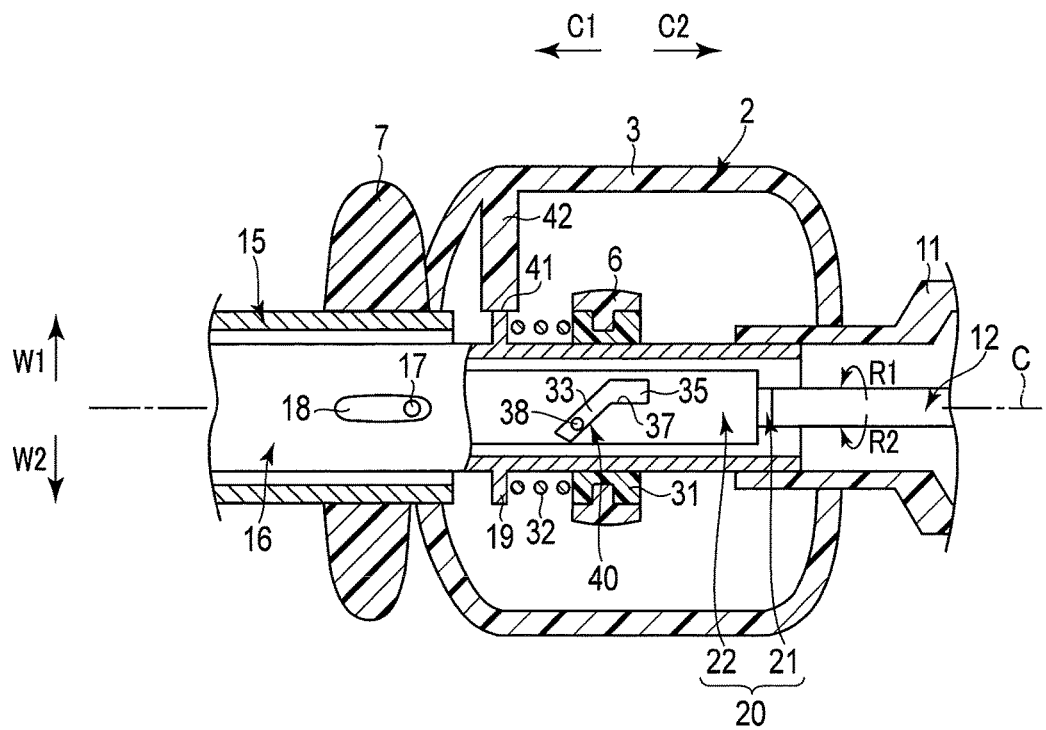
FIG. 7 is a cross-sectional view which schematically illustrates the internal configuration of the housing according to the modification of the first embodiment, in a state in which the engaging projection is located in a first guide groove.
Figure 8:
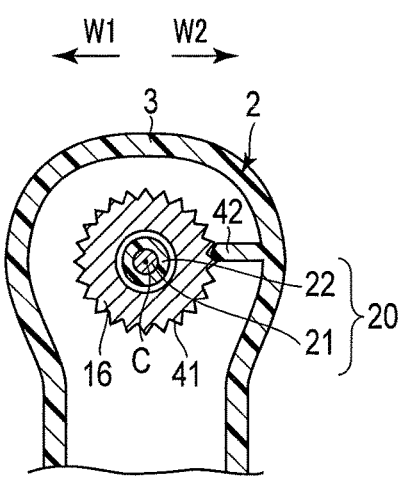
FIG. 8 is a cross-sectional view which schematically illustrates a cross section which is perpendicular to the longitudinal axis and passes through an irregular surface portion, in a state in which the engaging projection according to the modification of the first embodiment is located in the first guide groove.

In the meantime, in one modification of the first embodiment, which is illustrated in FIG. 6 to FIG. 8, an irregular surface portion 41 extends on an outer peripheral surface of the movable shaft 16 around the longitudinal axis C. FIG. 6 and FIG. 7 illustrate an internal configuration of the housing 2 by a cross section which is parallel (substantially parallel) to the longitudinal axis C and is parallel (substantially parallel) to the width direction of the housing 2 (a direction indicated by an arrow W1 and an arrow W2 in each of FIG. 6 to FIG. 8). In addition, FIG. 6 illustrates a state in which the engaging projection 38 is located in the second guide groove 35, and FIG. 7 illustrates a state in which the engaging projection 38 is located in the first guide groove 33. In the present modification, the irregular surface portion 41 is provided on the receiving portion 19 of the movable shaft 16, and extends over the entire circumference around the longitudinal axis C. FIG. 8 illustrates the internal configuration of the housing 2, and illustrates a cross section perpendicular (substantially perpendicular) to the longitudinal axis C passing through the irregular surface portion 41, in a state in which the engaging projection 38 is located in the first guide groove 33. In addition, in the present modification, an engaging piece 42 is formed, which projects from the inner peripheral surface of the housing 2 (the inner peripheral surface of the housing main body 3) toward the inner peripheral side.

As illustrated in FIG. 6, in the state in which the engaging projection 38 is located in the second guide groove 35 (i.e. the state in which the second gripper 27 is located in the spaced position), the irregular surface portion 41 is located apart from the engaging piece 42 in a direction along the longitudinal axis C. On the other hand, if the movable shaft 16 moves to the distal side and the engaging projection 38 moves to the first guide groove 33, the irregular surface portion 41 is located at substantially the same positon as the engaging piece 42 in the direction along the longitudinal axis C, and the engaging piece 42 is engaged with the irregular surface portion 41, as illustrated in FIG. 7 and FIG. 8. In the state in which the irregular surface portion 41 is engaged with the engaging piece 42, the movable shaft 16 is movable along the longitudinal axis C relative to the housing 2, but the rotation of the movable shaft 16 around the longitudinal axis C relative to the housing 2 is restricted. Incidentally, in the present modification, the dimension of the engaging piece 42 in the direction along the longitudinal axis C is substantially equal to the dimension of the first guide groove 33 in the direction along the longitudinal axis C.

As described above in the first embodiment, by the engaging projection 38 moving to the distal side in the first guide groove 33, the extension unit 20 rotates to the one side around the longitudinal axis C (first periaxial direction) relative to the sheath 15 and movable shaft 16 by the component element of the pushing force from the engaging projection 38 to the extension unit 20 toward the one side around the longitudinal axis C (the arrow R1 side in each of FIG. 6 and FIG. 7). On the other hand, by the engaging projection 38 moving to the proximal side in the first guide groove 33, the extension unit 20 rotates to the other side around the longitudinal axis C (second periaxial direction) relative to the sheath 15 and movable shaft 16 by the component element of the pushing force from the engaging projection 38 to the extension unit 20 toward the other side around the longitudinal axis C (the arrow R2 side in each of FIG. 6 and FIG. 7). When the extension unit 20 is rotating relative to the movable shaft 16 and sheath 15, reactive force to the pushing force from the engaging projection 38 to the extension unit 20 acts on the movable shaft 16 toward the side opposite to the rotational direction of the extension unit 20 around the longitudinal axis C.

In the present modification, in the state in which the engaging projection 38 is located in the first guide groove 33, the irregular surface portion 41 of the movable shaft 16 is engaged with the engaging piece 42, and the rotation of the movable shaft 16 around the longitudinal axis C relative to the housing 2 is restricted. Thus, even if the reactive force to the pushing force from the engaging projection 38 to the extension unit 20 acts on the movable shaft 16 by the engaging projection 38 moving in the first guide groove 33, it is possible to effectively prevent the movable shaft 16 (including the sheath 15 and rotary knob 7) from rotating to the side opposite to the rotational direction of the extension unit 20 relative to the housing 2. Accordingly, in the present modification, a rotation restriction unit is formed by the irregular surface portion 41 and engaging piece 42. The rotation restriction unit restricts the rotation of the movable shaft 16 around the longitudinal axis C relative to the housing 2 due to the reactive force to the pushing force from the engaging projection 38 to the extension unit 20.

In addition, as described above in the first embodiment, in the state in which the engaging projection 38 is located in the second guide groove 35, the angular position of the movable shaft 16 around the longitudinal axis C relative to the housing 2 varies by rotating the movable shaft 16 around the longitudinal axis C together with the rotary knob 7 and sheath 15. It should be noted, however, that in the present modification, the irregular surface portion 41 extends over the entire circumference of the outer peripheral surface of the movable shaft 16 around the longitudinal axis C (in the circumferential direction). Thus, regardless of the angular position of the movable shaft 16 around the longitudinal axis C relative to the housing 2, the engaging piece 42 is engaged with the irregular surface portion 41 in the state in which the engaging projection 38 is located in the first guide groove 33. Accordingly, in the present modification, regardless of the angular position of the movable shaft 16 around the longitudinal axis C relative to the housing 2, it is possible to effectively prevent the movable shaft 16 from rotating around the longitudinal axis C relative to the housing 2, due to the reactive force to the pushing force from the engaging projection 38 to the extension unit 20.

Second Embodiment

Next, a second embodiment of the present invention will be described with reference to FIG. 9 and FIG. 10. In the meantime, in the second embodiment, the configuration of the first embodiment is modified as described below. Incidentally, the same parts as in the first embodiment are denoted by like reference numerals, and a description thereof is omitted.

Figure 9:
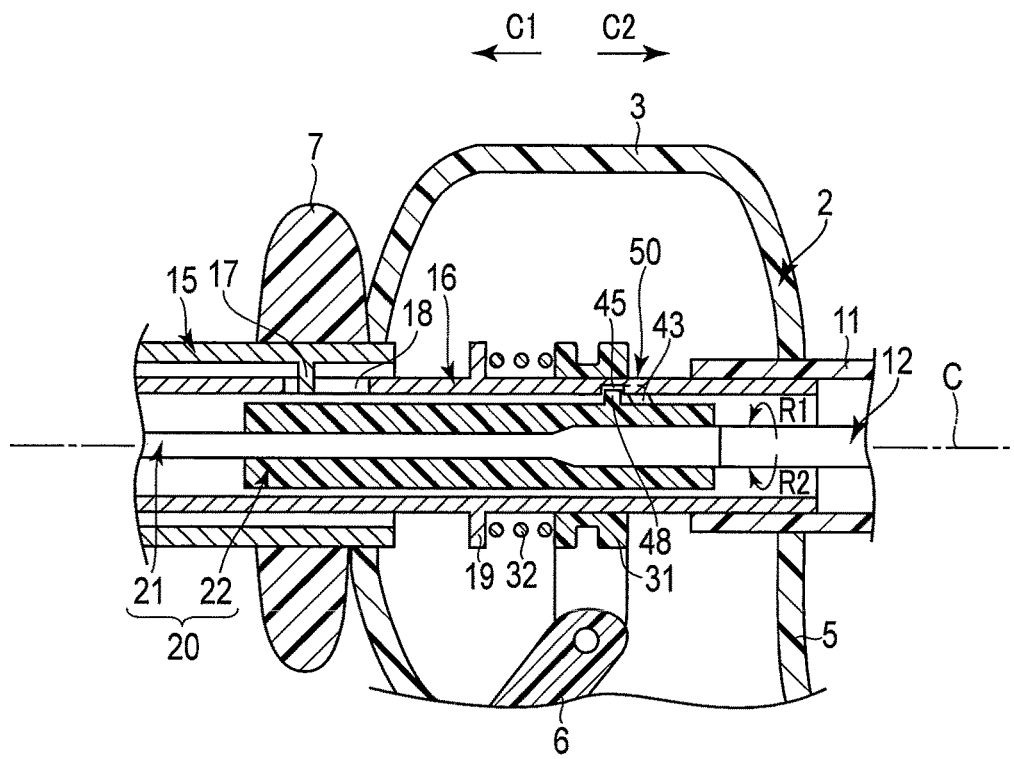
FIG. 9 is a cross-sectional view which schematically illustrates an internal configuration of a housing according to a second embodiment by a cross section perpendicular to the width direction of the housing.
Figure 10:
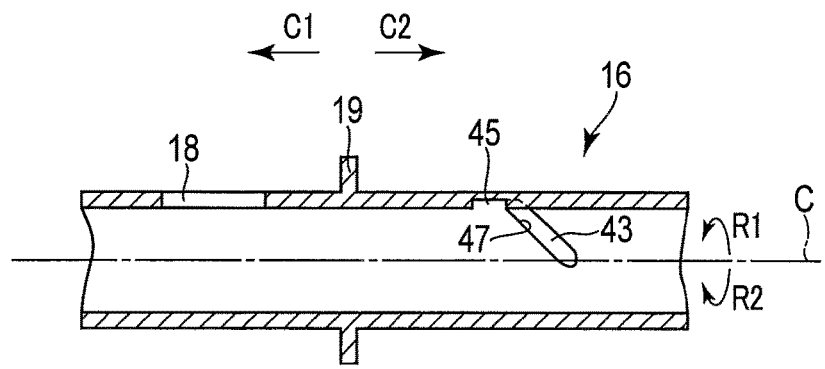
FIG. 10 is a cross-sectional view which schematically illustrates a configuration of a movable shaft according to the second embodiment.

FIG. 9 illustrates an internal configuration of a housing 2 by a cross section perpendicular to the width direction of the housing 2. FIG. 10 is a view illustrating a configuration of a movable shaft 16. As illustrated in FIG. 9 and FIG. 10, in the present embodiment, the engaging projection 38 is not provided on the inner peripheral surface of the movable shaft 16. Instead, a first guide groove 43 and a second guide groove 45, which are recessed toward the outer peripheral side, are formed by a groove forming surface (groove forming portion) 47 on the inner peripheral surface of the movable shaft 16. The first guide groove 43 extends from one side (an arrow R1 side in each of FIG. 9 and FIG. 10) toward the other side (an arrow R2 side in each of FIG. 9 and FIG. 10) around the longitudinal axis C as extending from the proximal side toward the distal side. Specifically, the first guide groove 43 extends in an inclined state relative to the longitudinal axis C. In the present embodiment, too, the first guide groove 43 extends over an angle range of at least 90° around the longitudinal axis C. The second guide groove 45 extends along the longitudinal axis C (in a non-inclined state relative to the longitudinal axis C), and is continuous with a distal end (one end) of the first guide groove 43.

In addition, in the present embodiment, the first guide groove 33 and second guide groove 35 are not provided on the outer peripheral surface of the holding member 22 (the outer peripheral surface of the extension unit 20). Instead, an engaging projection (engaging portion) 48, which projects toward the outer peripheral side, is formed on the outer peripheral surface of the holding member 22. The engaging projection 48 is provided in the holding member 22 at a position where the engaging projection 48 is engageable with the first guide groove 43 and second guide groove 45. In the present embodiment, by opening or closing the handle 6 relative to the grip 5, the movable shaft 16 moves along the longitudinal axis X, and thereby the first guide groove 43 and second guide groove 45 move relative to the engaging projection 48. Thereby, in accordance with the movement of the movable shaft 16 along the longitudinal axis C, the position of the engaging projection 48 varies in the first guide groove 43 and second guide groove 45.

In the state in which the second gripper 27 is located in the spaced position relative to the first gripper 26, the engaging projection 48 is located in the second guide groove 45. In the state in which the engaging projection 48 is located in the second guide groove 45, although the movable shaft 16 is movable along the longitudinal axis C relative to the extension unit 20, the rotation of the movable shaft 16 around the longitudinal axis C relative to the extension unit 20 is restricted. Accordingly, in the state in which the engaging projection 48 is located in the second guide groove 45, by the movable shaft 16 rotating around the longitudinal axis C together with the rotary knob 7 and sheath 15, rotational driving force is transmitted from the movable shaft 16 to the holding member 22 through the engaging projection 48 in the second guide groove 45, and the extension unit 20 (vibration transmitting member 21 and holding member 22) rotates together with the movable shaft 16 around the longitudinal axis C. Accordingly, in this embodiment, too, in the state in which the second gripper 27 is located in the spaced position relative to the first gripper 26 (the state in which the engaging projection 48 is located in the second guide groove 45), the sheath 15, movable shaft 16, extension unit 20 and second gripper 27 rotate together around the longitudinal axis C by rotating the rotary knob 7.

In the present embodiment, in accordance with the movement of the movable shaft 16 to the distal side relative to the sheath 15 and extension unit 20 and the rotation of the second gripper 27 toward the closed position, the first guide groove 43 and second guide groove 45 move from the proximal side to the distal side relative to the engaging projection 48. By the first guide groove 43 moving to the distal side relative to the engaging projection 48 in the state in which the engaging projection 48 is located in the first guide groove 43, pushing force acts on the engaging projection 48 of the extension unit 20 from the outer edge of the first guide groove 43, and the pushing force is decomposed into a component element to the distal side and a component element to one side around the longitudinal axis C (the arrow R1 side in each of FIG. 9 and FIG. 10). By the component element of the pushing force from the outer edge of the first guide groove 43 to the one side around the longitudinal axis C (first periaxial direction), the extension unit 20 rotates to the one side around the longitudinal axis C (first periaxial direction) relative to the sheath 15 and movable shaft 16. Thereby, the first gripper 26 rotates toward the one side around the rotational axis C relative to the second gripper 27.

In addition, in accordance with the movement of the movable shaft 16 to the proximal side relative to the sheath 15 and extension unit 20 and the rotation of the second gripper 27 toward the spaced position, the first guide groove 43 and second guide groove 45 move from the distal side to the proximal side relative to the engaging projection 48. By the first guide groove 43 moving to the proximal side relative to the engaging projection 48 in the state in which the engaging projection 48 is located in the first guide groove 43, pushing force acts on the extension unit 20 from the outer edge of the first guide groove 43, and the pushing force is decomposed into a component element to the proximal side and a component element to the other side around the longitudinal axis C (the arrow R2 side in each of FIG. 9 and FIG. 10). By the component element of the pushing force from the outer edge of the first guide groove 43 to the other side around the longitudinal axis C (second periaxial direction), the extension unit 20 rotates to the other side around the longitudinal axis C (second periaxial direction) relative to the sheath 15 and movable shaft 16. Thereby, the first gripper 26 rotates toward the other side around the rotational axis C relative to the second gripper 27.

As described above, in the present embodiment, the position of the engaging projection (engaging portion) 48 in the first guide groove 43 varies in accordance with the movement of the movable shaft 16 along the longitudinal axis C. Thereby, a linear movement of the movable shaft 16 is converted to a rotational movement of the extension unit 20 (vibration transmitting member 21 and holding member 22) around the longitudinal axis C relative to the movable shaft 16. By the rotational movement of the extension unit 20 relative to the movable shaft 16, the first gripper 26 rotates about the longitudinal axis C relative to the second gripper 27. Accordingly, in the present embodiment, too, an interlocking actuator 50 is formed by the groove forming surface (groove forming portion) 47 and engaging projection (engaging portion) 48. The interlocking actuator 50 rotates the vibration transmitting member 21, which includes the first gripper 26, about the longitudinal axis C relative to the second gripper 27, in interlock with the movement of the movable shaft 16 along the longitudinal axis C (i.e. the movement of the second gripper 27 between the closed position and the spaced position). Specifically, by the interlocking actuator 50, the first gripper 26 moves (rotates) in interlock with the movement of the second gripper 27 between the closed positon and the spaced position.

As described above, in the present embodiment, like the first embodiment, since the interlocking actuator 50 is provided, when the first gripper 26 and second gripper 27 are closed with respect to each other by the movement of the movable shaft 16 to the distal side, the spacing distance between the first gripper 26 and second griper 27 decreases due to the movement of the second gripper 27 toward the closed position, and also the spacing distance between the first gripper 26 and second griper 27 decreases due to the rotational movement (motion) of the first gripper 26 relative to the second gripper 27 toward the one side around the longitudinal axis C. In addition, when the first gripper 26 and second gripper 27 are opened with respect to each other by the movement of the movable shaft 16 to the proximal side, the spacing distance between the first gripper 26 and second griper 27 increases due to the movement of the second gripper 27 toward the spaced position, and also the spacing distance between the first gripper 26 and second griper 27 increases due to the rotational movement of the first gripper 26 relative to the second gripper 27 toward the other side around the longitudinal axis C. Therefore, in the present embodiment, the same function and advantageous effects as in the first embodiment can be obtained.

Modification of the Second Embodiment

In the meantime, in the configuration in which, as in the second embodiment, the movable shaft 16 is provided with the first guide groove 43 and second guide groove 45 and the extension unit 20 is provided with the engaging projection 48, the rotation restriction unit (irregular surface portion 41 and engaging piece 42) described above in the modification of FIG. 6 to FIG. 8 may be provided. In this case, in the state in which the engaging projection 48 is located in the second guide groove 45 (i.e. the state in which the second gripper 27 is located in the spaced position), the irregular surface portion 41 is located apart from the engaging piece 42 in the direction along the longitudinal axis C. In addition, in the state in which the engaging projection 48 is located in the first guide groove 43, the engaging piece 42 is engaged with the irregular surface portion 41.

Third Embodiment

Next, a third embodiment of the present invention will be described with reference to FIG. 11 and FIG. 12. In the meantime, in the third embodiment, the configuration of the first embodiment is modified as described below. Incidentally, the same parts as in the first embodiment are denoted by like reference numerals, and a description thereof is omitted.

Figure 11:
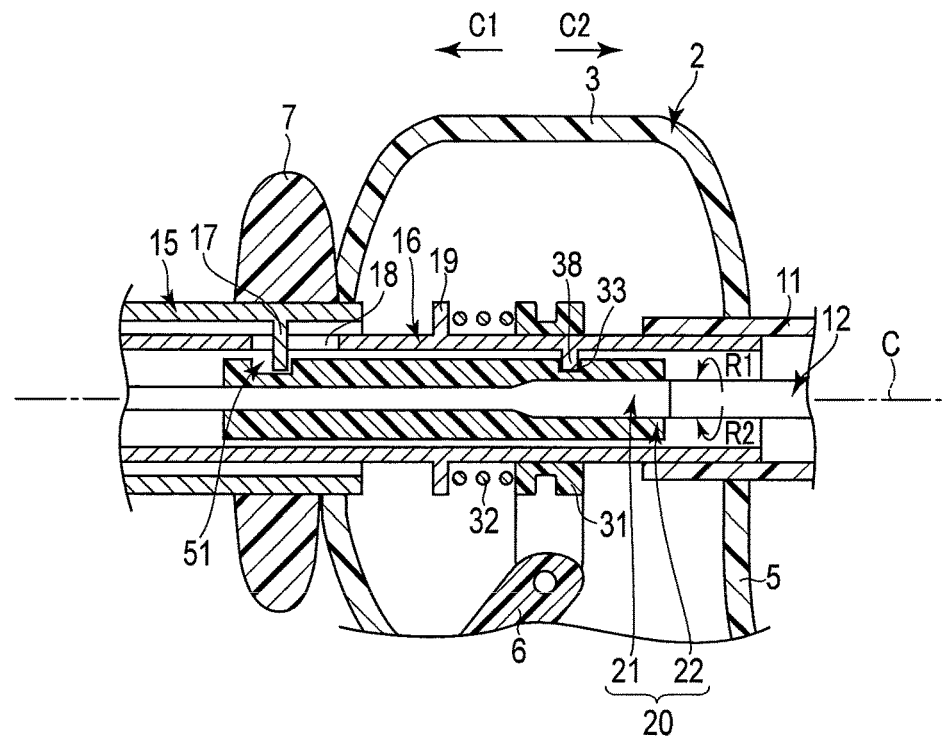
FIG. 11 is a cross-sectional view which schematically illustrates an internal configuration of a housing according to a third embodiment by a cross section perpendicular to the width direction of the housing.
Figure 12:
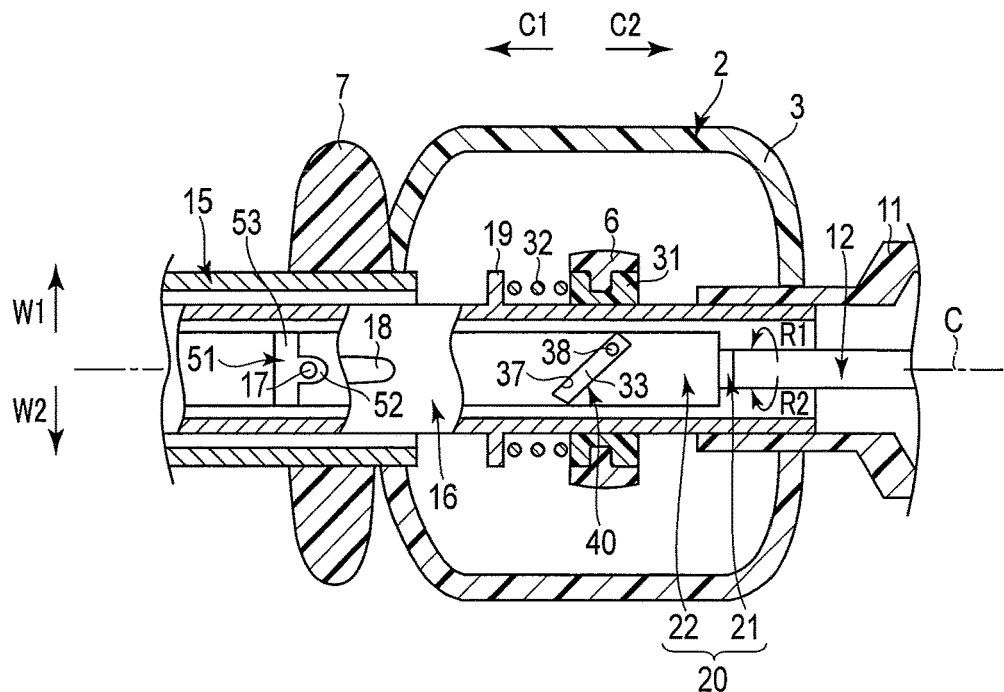
FIG. 12 is a cross-sectional view which schematically illustrates the internal configuration of the housing according to the third embodiment by a cross section which is parallel to the longitudinal axis and is parallel to the width direction of the housing.

FIG. 11 illustrates a cross section perpendicular (substantially perpendicular) to the width direction of a housing 2 (a direction indicated by an arrow W1 and an arrow W2 in FIG. 12). FIG. 12 illustrates a cross section which is parallel (substantially parallel) to the longitudinal axis C and is parallel (substantially parallel) to the width direction of the housing 2. As illustrated in FIG. 11 and FIG. 12, in the present embodiment, only the first guide groove 33 is formed by the groove forming surface (groove forming portion) 37 on the outer peripheral surface of the extension unit (holding member 22), and the second guide groove 35 is not formed. In addition, in this embodiment, an engaging projection (engaging portion) 38, which is engageable with the first guide groove 33, is formed on the inner peripheral surface of the movable shaft 16, and the engaging projection (engaging portion) 38 moves in the first guide groove 33 in accordance with the movement of the movable shaft 16 along the longitudinal axis C.

In the present embodiment, instead of the second guide groove 35, an engaging groove 51 is formed on the outer peripheral surface of the holding member 22. In this embodiment, the engaging groove 51 is located on the distal side with respect to the first guide groove 33. In this embodiment, the projection 17 of the sheath 15 is inserted through the engaging hole 18 of the movable shaft 16, and is inserted in the engaging groove 51 of the holding member 22. Furthermore, in this embodiment, the rotary knob 7 and sheath 15 are movable along the longitudinal axis C relative to the extension unit 20. By moving the rotary knob 7 and sheath 15 along the longitudinal axis C relative to the extension unit 20 by a manual operation or the like, the projection 17 moves along the longitudinal axis C in the engaging hole 18 and engaging groove 51. The engaging groove 51 includes an axial extension portion 52 which extends along the longitudinal axis C, and a periaxial extension portion 53 which extends over the entire circumference around the longitudinal axis C. A distal end of the axial extension portion 52 is continuous with the periaxial extension portion 53. By moving the rotary knob 7 and sheath 15 relative to the extension unit 20 along the longitudinal axis C, the position of the projection 17 changes between the state in which the projection 17 is located in the axial extension portion 52 and the state in which the projection 17 is located in the periaxial extension portion 53.

When the rotary knob 7 is rotated and the angular position of the second gripper 27 around the longitudinal axis C is adjusted, the projection 17 is located in the axial extension portion 52. Although the projection 17 is movable in the axial extension portion 52 along the longitudinal axis C, the movement of the projection 17 around the longitudinal axis C is restricted by the edge of the axial extension portion 52. Thus, in the state in which the projection 17 is located in the axial extension portion 52, the sheath 15 is movable relative to the extension unit 20 along the longitudinal axis C, but the rotation of the sheath 15 relative to the extension unit 20 around the longitudinal axis C is restricted. Accordingly, by the rotary knob 7 and sheath 15 rotating, the extension unit 20 rotates together with the movable shaft 16, rotary knob 7 and sheath 15 around the longitudinal axis C. Thus, in the state in which the projection 17 is located in the axial extension portion 52, the sheath 15, movable shaft 16, extension unit 20 and second gripper 27 rotate together around the longitudinal axis C by rotating the rotary knob 7.

On the other hand, when the movable shaft 16 is moved along the longitudinal axis C by opening or closing the handle 6 relative to the grip 5, the projection 17 is located in the periaxial extension portion 53. In the periaxial extension portion 53, the movement of the projection 17 around the longitudinal axis C is not restricted. Thus, in the state in which the projection 17 is located in the periaxial extension portion 53, the sheath 15 is rotatable relative to the extension unit 20 around the longitudinal axis C.

Thus, like the first embodiment, in the state in which the projection 17 is located in the periaxial extension portion 53, by the engaging projection 38 moving in the first guide groove 33 to the distal side, the extension unit 20 rotates to the one side around the longitudinal axis C (first periaxial direction) relative to the sheath 15 and movable shaft 16 by the component element of the pushing force from the engaging projection 38 to the extension unit 20 toward the one side around the longitudinal axis C (an arrow R1 side in each of FIG. 11 and FIG. 12). In addition, by the engaging projection 38 moving to the proximal side in the first guide groove 33, the extension unit 20 rotates to the other side around the longitudinal axis C (second periaxial direction) relative to the sheath 15 and movable shaft 16 by the component element of the pushing force from the engaging projection 38 to the extension unit 20 toward the other side around the longitudinal axis C (an arrow R2 side in each of FIG. 11 and FIG. 12).

Specifically, like the first embodiment, in the state in which the projection 17 is located in the periaxial extension portion 53, the position of the engaging projection (engaging portion) 38 in the first guide groove 33 varies in accordance with the movement of the movable shaft 16 along the longitudinal axis C. Thereby, by the interlocking actuator 40, a linear movement of the movable shaft 16 is converted to a rotational movement of the extension unit 20 (vibration transmitting member 21 and holding member 22) around the longitudinal axis C relative to the movable shaft 16. By the rotational movement of the extension unit 20 relative to the movable shaft 16, the first gripper 26 rotates about the longitudinal axis C relative to the second gripper 27. Therefore, in the present embodiment, the same function and advantageous effects as in the first embodiment can be obtained.

Modifications of the Third Embodiment

Figure 13:
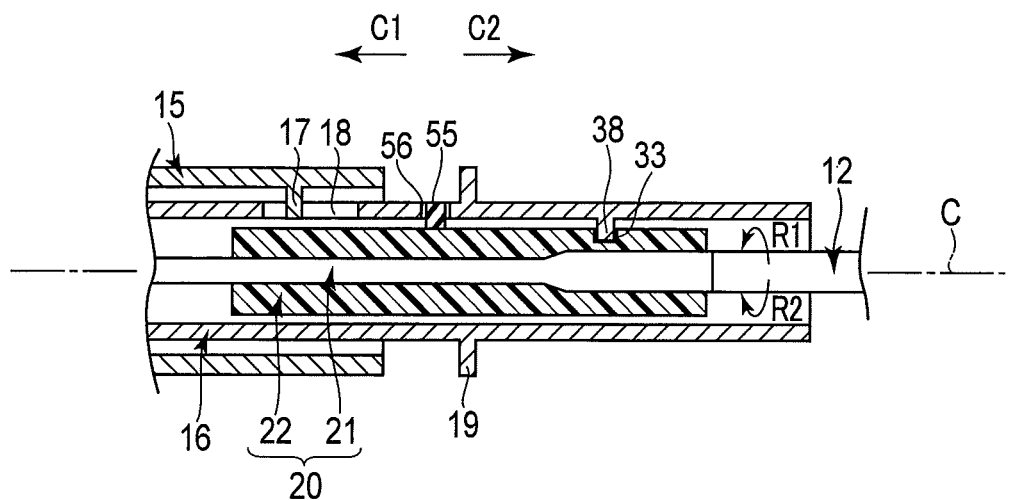
FIG. 13 is a cross-sectional view which schematically illustrates a configuration of a sheath, a movable shaft and an extension unit according to one modification of the third embodiment.

In the meantime, as illustrated in FIG. 13 as one modification of the third embodiment, an insertion projection 55, which projects from the outer peripheral surface of the holding member 22 (extension unit 20), may be provided in place of the engaging groove 51. FIG. 13 illustrates a configuration of the sheath 15, movable shaft 16 and extension unit 20 by a cross section perpendicular to the width direction of the housing 2. In the present modification, as illustrated in FIG. 13, an insertion hole 56, in which the insertion projection 55 can be inserted, is formed in the movable shaft 16. In addition, the insertion projection 55 is formed of an elastic material, and the insertion projection 55 is inserted in the insertion hole 56 in the state in which the second gripper 27 is located in the spaced position. Incidentally, in this modification, like the third embodiment, the extension unit 20 is not provided with the second guide groove 35.

The movement of the insertion projection 55 around the longitudinal axis C is restricted in the insertion hole 56. Thus, in the state in which the insertion projection 55 is inserted in the insertion hole 56, the rotation of the movable shaft 16 around the longitudinal axis C relative to the extension unit 20 is restricted. Accordingly, by the rotary knob 7 and sheath 15 rotating, the extension unit 20 rotates around the longitudinal axis C together with the movable shaft 16, rotary knob 7 and sheath 15. Thus, in the state in which the second gripper 27 is located in the spaced position (i.e. the state in which the insertion projection 55 is inserted in the insertion hole 56), the sheath 15, movable shaft 16, extension unit 20 and second gripper 27 rotate together around the longitudinal axis C by rotating the knob 7.

In addition, by closing the handle 6 relative to the grip 5 from the state in which the second gripper 27 is located in the spaced position, and moving the movable shaft 16 to the distal side relative to the extension unit 20, the insertion projection 55 is pushed by the edge of the insertion hole 56, and the insertion projection 55 elastically deforms. By the insertion projection 55 elastically deforming, the insertion projection 55 is drawn out from the insertion hole 56. In the state in which the insertion projection 55 is drawn out from the insertion hole 56, the movable shaft 16 is rotatable around the longitudinal axis C relative to the extension unit 20. Accordingly, by moving the second gripper 27 from the spaced position toward the closed position, the movable shaft 16 becomes rotatable around the longitudinal axis C relative to the extension unit 20.

Thus, in the state in which the position of the engaging projection (engaging portion) 38 is varying in the first guide groove 33 in accordance with the movement of the movable shaft 16 along the longitudinal axis C, the insertion projection 55 is drawn out from the insertion hole 56, and the movable shaft 16 becomes rotatable around the longitudinal axis C relative to the extension unit 20. Accordingly, by the position of the engaging projection (engaging portion) 38 varying in the first guide groove 33 in accordance with the movement of the movable shaft 16 along the longitudinal axis C, a linear movement of the movable shaft 16 is converted by the interlocking actuator 40 to a rotational movement of the extension unit 20 (vibration transmitting member 21 and holding member 22) around the longitudinal axis C relative to the movable shaft 16. By the rotational movement of the extension unit 20 relative to the movable shaft 16, the first gripper 26 rotates about the longitudinal axis C relative to the second gripper 27. Therefore, in the present modification, the same function and advantageous effects as in the third embodiment can be obtained.

In the meantime, in the present modification, by the movable shaft 16 moving to the proximal side, and by the second gripper 27 being located in the spaced position, the insertion projection 55 elastically restores. Thereby, the insertion projection 55 is inserted in the insertion hole 56, and the rotation of the movable shaft 16 around the longitudinal axis C relative to the extension unit 20 is restricted.

Additionally, in one modification, in the configuration in which, like the second embodiment, the movable shaft 16 is provided with the first guide groove 43, and the extension unit (holding member 22) is provided with the engaging projection 48, the second guide groove 45 may not be provided in the movable shaft 16. In this case, like the third embodiment, the engaging groove 51 may be provided in the holding member 22, or, like the modification of FIG. 13, the insertion projection 55 may be provided in the holding member 22, and the insertion hole 56 may be provided in the movable shaft 16.

Fourth Embodiment

Next, a fourth embodiment of the present invention will be described with reference to FIG. 14. In the meantime, in the fourth embodiment, the configuration of the first embodiment is modified as described below. Incidentally, the same parts as in the first embodiment are denoted by like reference numerals, and a description thereof is omitted.

Figure 14:
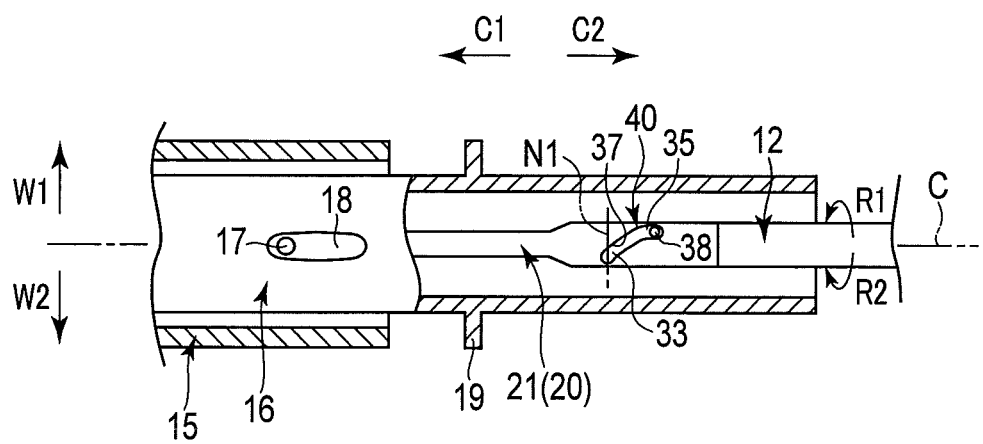
FIG. 14 is a cross-sectional view which schematically illustrates a configuration of a sheath, a movable shaft and an extension unit according to a fourth embodiment.

FIG. 14 illustrates a sheath 15, movable shaft 16 and extension unit 20 by a cross section which is parallel (substantially parallel) to the longitudinal axis C and is parallel (substantially parallel) to the width direction of the housing 2 (a direction indicated by an arrow W1 and an arrow W2 in FIG. 14). As illustrated in FIG. 14, in the present embodiment, the extension unit 20 is not provided with the holding member 22. In addition, on the outer peripheral surface of the vibration transmitting member 21, a first guide groove 33 and a second guide groove 35, which are similar to those in the first embodiment, are formed by a groove forming surface (groove forming portion) 37. In addition, an engaging projection (engaging portion) 38, which is engageable with the first guide groove 33 and second guide groove 35, is provided on the inner peripheral surface of the movable shaft 16. Accordingly, in the present embodiment, the same interlocking actuator 40 as in the first embodiment is formed.

Thus, in the present embodiment, like the first embodiment, the position of the engaging projection (engaging portion) 38 in the first guide groove 33 varies in accordance with the movement of the movable shaft 16 along the longitudinal axis C. Thereby, by the interlocking actuator 40, a linear movement of the movable shaft 16 is converted to a rotational movement of the extension unit 20 (vibration transmitting member 21) around the longitudinal axis C relative to the movable shaft 16. By the rotational movement of the extension unit 20 relative to the movable shaft 16, the first gripper 26 rotates about the longitudinal axis C relative to the second gripper 27. Therefore, in the present embodiment, the same function and advantageous effects as in the first embodiment can be obtained.

In addition, in the present embodiment, in the state in which the vibration transmitting member 21 is transmitting ultrasonic vibration toward the first gripper 26 (i.e. the state in which the vibration transmitting member 21 is longitudinally vibrating in a predetermined frequency range (e.g. 46 kHz to 48 kHz)), one (N1) of vibration nodes in the direction along the longitudinal axis C is located in a range in which the first guide groove 33 extends. As described above in the present embodiment, in the state in which the vibration transmitting member 21 is transmitting ultrasonic vibration toward the first gripper 26, the second gripper 27 moves from the spaced position toward the closed position, and the engaging projection 38 is located in the first guide groove 33. In addition, the engaging projection 38 abuts on the outer edge of the first guide groove 33, and exerts pushing force on the vibration transmitting member 21. Here, since the vibration node N1 is located in the first guide groove 33, the amplitude of vibration (longitudinal vibration) becomes zero or very small in the first guide groove 33 of the vibration transmitting member 21. Thus, even if ultrasonic vibration is transmitted in the vibration transmitting member 21 in the state in which the engaging projection 38 abuts on the outer edge of the first guide groove 33, ultrasonic vibration is hardly transmitted from the vibration transmitting member 21 to the movable shaft 16 via the engaging projection 38.

Modification of the Fourth Embodiment

Figure 15:
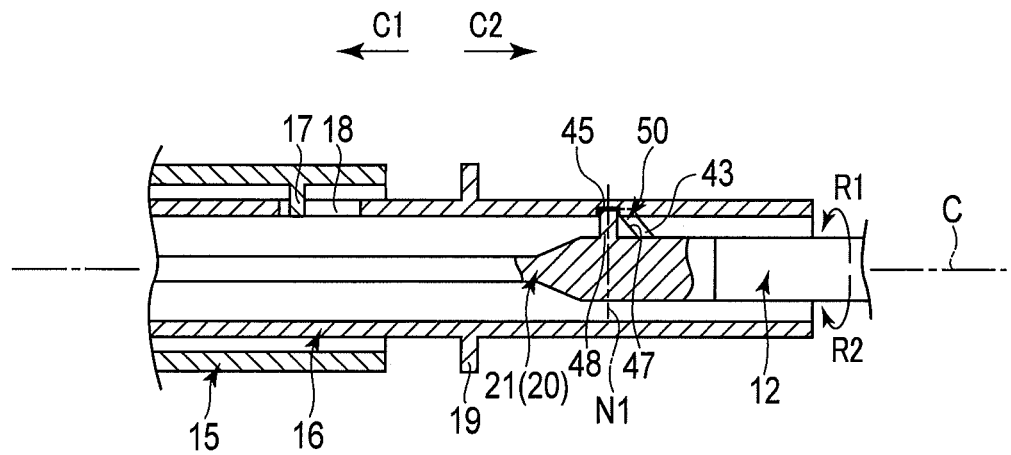
FIG. 15 is a cross-sectional view which schematically illustrates a configuration of a sheath, a movable shaft and an extension unit according to one modification of the fourth embodiment.

In addition, in one modification of the fourth embodiment, which is illustrated in FIG. 15, an interlocking actuator 50, which is the same as in the second embodiment, is provided in the configuration in which, like the fourth embodiment, the extension unit 20 is not provided with the holding member 22. Specifically, in the present modification, on the inner peripheral surface of the movable shaft 16, a first guide groove 43 and a second guide groove 45, which are the same as those in the second embodiment, are formed by a groove forming surface (groove forming portion) 47. An engaging projection (engaging portion) 48, which is engageable with the first guide groove 43 and second guide groove 45, is provided on the outer peripheral surface of the vibration transmitting member 21. Incidentally, FIG. 15 illustrates the sheath 15, movable shaft 16 and extension unit 20 by a cross section perpendicular (substantially perpendicular) to the width direction of the housing 2.

In the present modification, like the second embodiment, the position of the engaging projection (engaging portion) 48 in the first guide groove 43 varies in accordance with the movement of the movable shaft 16 along the longitudinal axis C. Thereby, by the interlocking actuator 50, a linear movement of the movable shaft 16 is converted to a rotational movement of the extension unit 20 (vibration transmitting member 21) around the longitudinal axis C relative to the movable shaft 16. In addition, by the rotational movement of the extension unit 20 relative to the movable shaft 16, the first gripper 26, rotates about the longitudinal axis C relative to the second gripper 27. Therefore, in the present modification, the same function and advantageous effects as in the above-described embodiments, etc. can be obtained.

Moreover, in the present modification, in the state in which the vibration transmitting member 21 is transmitting ultrasonic vibration toward the first gripper 26 (i.e. the state in which the vibration transmitting member 21 is longitudinally vibrating in a predetermined frequency range (e.g. 46 kHz to 48 kHz)), one (N1) of vibration nodes in the direction along the longitudinal axis C is located at the engaging projection (engaging portion) 48. As described in the second embodiment, in the state in which the vibration transmitting member 21 is transmitting ultrasonic vibration toward the first gripper 26, the second gripper 27 moves from the spaced position toward the closed position, and the engaging projection 48 is located in the first guide groove 43. In addition, the engaging projection 48 abuts on the outer edge of the first guide groove 43, and receives pushing force from the outer edge of the first guide groove 43. Here, since the vibration node N1 is located at the engaging projection 48, the amplitude of vibration (longitudinal vibration) becomes zero or very small at the engaging projection 48 of the vibration transmitting member 21. Thus, even if ultrasonic vibration is transmitted in the vibration transmitting member 21 in the state in which the engaging projection 48 abuts on the outer edge of the first guide groove 43, ultrasonic vibration is hardly transmitted from the vibration transmitting member 21 to the movable shaft 16 via the engaging projection 48.

Fifth Embodiment

Next, a fifth embodiment of the present invention will be described with reference to FIG. 16. In the meantime, in the fifth embodiment, the configuration of the fourth embodiment is modified as described below. Incidentally, the same parts as in the first embodiment are denoted by like reference numerals, and a description thereof is omitted.

Figure 16:
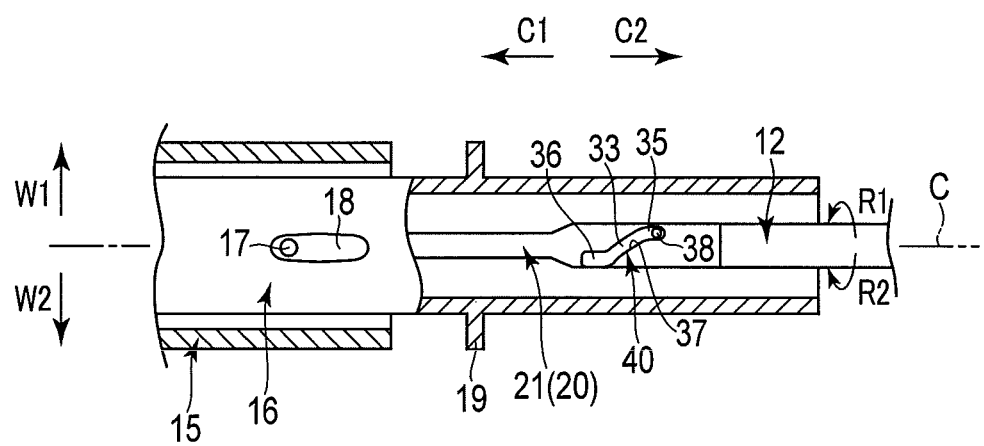
FIG. 16 is a cross-sectional view which schematically illustrates a configuration of a sheath, a movable shaft and an extension unit according to a fifth embodiment.

FIG. 16 illustrates a sheath 15, movable shaft 16 and extension unit 20 by a cross section which is parallel (substantially parallel) to the longitudinal axis C and is parallel (substantially parallel) to the width direction of the housing 2 (a direction indicated by an arrow W1 and an arrow W2 in FIG. 16). As illustrated in FIG. 16, in the present embodiment, like the fourth embodiment, the extension unit 20 is not provided with the holding member 22. In addition, like the fourth embodiment, on the outer peripheral surface of the vibration transmitting member 21, a first guide groove 33 and a second guide groove 35 are formed by a groove forming surface (groove forming portion) 37. In addition, an engaging projection (engaging portion) 38, which is engageable with the first guide groove 33 and second guide groove 35, is provided on the inner peripheral surface of the movable shaft 16. Accordingly, in the present embodiment, like the fourth embodiment, the position of the engaging projection (engaging portion) 38 in the first guide groove 33 varies in accordance with the movement of the movable shaft 16 along the longitudinal axis C. Thereby, by the interlocking actuator 40, a linear movement of the movable shaft 16 is converted to a rotational movement of the extension unit 20 (vibration transmitting member 21) around the longitudinal axis C relative to the movable shaft 16. By the rotational movement of the extension unit 20 relative to the movable shaft 16, the first gripper 26 rotates about the longitudinal axis C relative to the second gripper 27. Therefore, in the present embodiment, the same function and advantageous effects as in the above-described embodiments, etc. can be obtained.

However, in the interlocking actuator 40 of the present embodiment, a third guide groove 36 is formed by the groove forming surface 37 on the outer peripheral surface of the vibration transmitting member 21 (extension unit 20), and the engaging projection 38 is engageable with the third guide groove 36. The third guide groove 36 extends along the longitudinal axis C and is, in this embodiment, continuous with the distal end (other end) of the first guide groove 33. In the present embodiment, by moving the second gripper 27 from the spaced position to the closed position, the engaging projection 38 moves from the second guide groove 35 to the third guide groove 36 via the first guide groove 33. Accordingly, in the state in which the second gripper 27 is located in the closed position or nearby there, the engaging projection 38 is located in the third guide groove 36. In addition, the dimension (width dimension) of the third guide groove 36 around the longitudinal axis C has such largeness that the engaging projection 38 does not abut. Thus, in the state in which the engaging projection 38 is located in the third guide groove 36, pushing force or the like is prevented from acting between the engaging projection 38 and the outer edge of the third guide groove 36.

In the state in which the vibration transmitting member 21 is transmitting ultrasonic vibration toward the first gripper 26 (i.e. the state in which the treated target, which is grasped between the first gripper 26 and second gripper 27, is being treated by using ultrasonic vibration), the second gripper 27 moves to the closed position or nearby there, and the engaging projection 38 passes through the first guide groove 33 and is located in the third guide groove 36. In addition, in the third guide groove 36, abutment between the engaging projection 38 and the outer edge of the third guide groove 36 is prevented. Thus, even if ultrasonic vibration is transmitted in the vibration transmitting member 21 in the state in which the second gripper 27 is located in the closed position or nearby there, the ultrasonic vibration is hardly transmitted from the vibration transmitting member 21 to the movable shaft 16 via the engaging projection 38.

Modification of the Fifth Embodiment

Figure 17:
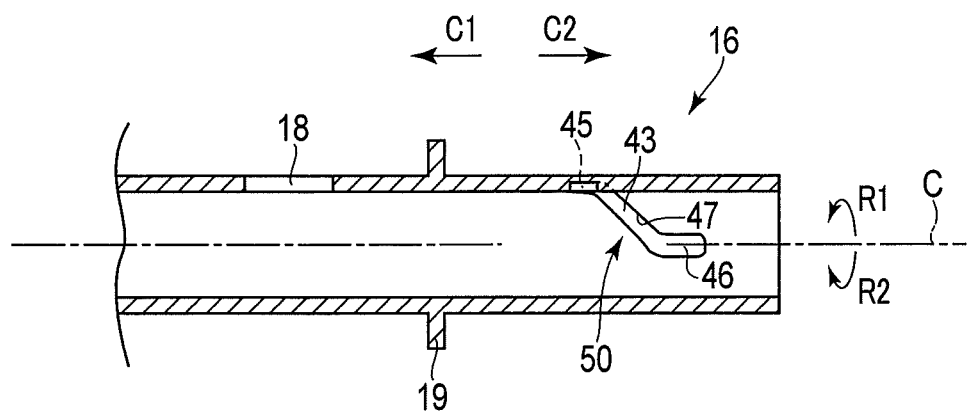
FIG. 17 is a cross-sectional view which schematically illustrates a configuration of a movable shaft according to one modification of the fifth embodiment.

In addition, in one modification of the fifth embodiment, which is illustrated in FIG. 17, like the fifth embodiment, the extension unit 20 is not provided with the holding member 22. In addition, like the modification of FIG. 15, on the inner peripheral surface of the movable shaft 16, a first guide groove 43 and a second guide groove 45 are formed by a groove forming surface (groove forming portion) 47. An engaging projection (engaging portion) 48, which is engageable with the first guide groove 43 and second guide groove 45, is provided on the outer peripheral surface of the vibration transmitting member 21. Thus, in this modification, like the modification of FIG. 15, the position of the engaging projection (engaging portion) 48 varies in the first guide groove 43 in accordance with the movement of the movable shaft 16 along the longitudinal axis C. Thereby, by the interlocking actuator 50, a linear movement of the movable shaft 16 is converted to a rotational movement of the extension unit 20 (vibration transmitting member 21) around the longitudinal axis C relative to the movable shaft 16. By the rotational movement of the extension unit 20 relative to the movable shaft 16, the first gripper 26 rotates about the longitudinal axis C relative to the second gripper 27. Therefore, in the present modification, the same function and advantageous effects as in the above-described embodiments, etc. can be obtained.

However, in the interlocking actuator 50 of the present modification, a third guide groove 46 is formed by the groove forming surface 47 on the inner peripheral surface of the movable shaft 16, and the engaging projection 48 is engageable with the third guide groove 46. The third guide groove 46 extends along the longitudinal axis C and is, in this modification, continuous with the proximal end (other end) of the first guide groove 43. In the present modification, by moving the second gripper 27 from the spaced position to the closed position, the second guide groove 45 and the first guide groove 43 pass by the engaging projection 48, and the third guide groove 46 moves up to the engaging projection 48. Accordingly, in the state in which the second gripper 27 is located in the closed position or nearby there, the engaging projection 48 is located in the third guide groove 46. In addition, the dimension (width dimension) of the third guide groove 46 around the longitudinal axis C has such largeness that the engaging projection 48 does not abut. Thus, in the state in which the engaging projection 48 is located in the third guide groove 46, pushing force or the like is prevented from acting between the engaging projection 48 and the outer edge of the third guide groove 46.

In the state in which the vibration transmitting member 21 is transmitting ultrasonic vibration toward the first gripper 26 (i.e. the state in which the treated target, which is grasped between the first gripper 26 and second gripper 27, is being treated by using ultrasonic vibration), the second gripper 27 moves to the closed position or nearby there, and the engaging projection 48 is located in the third guide groove 46. In addition, in the third guide groove 46, abutment between the engaging projection 48 and the outer edge of the third guide groove 46 is prevented. Thus, even if ultrasonic vibration is transmitted in the vibration transmitting member 21 in the state in which the second gripper 27 is located in the closed position or nearby there, the ultrasonic vibration is hardly transmitted from the vibration transmitting Member 21 to the movable shaft 16 via the engaging projection 48.

Modifications of the First Embodiment to the Fifth Embodiment

In the first embodiment to the fifth embodiment and the modifications thereof, the first gripper (26) is curved relative to the longitudinal axis (C). In addition, the interlocking actuator (40; 50) rotates the vibration transmitting member (21) relative to the second gripper (27) in a predetermined direction about the longitudinal axis (C) in interlock with the movement of the second gripper (27) to the spaced position. Thereby, the interlocking actuator (40; 50) increases the spacing distance between the first gripper (26) and second gripper (27) in accordance with the rotational movement of the first gripper (26) in the predetermined direction. If this configuration is included, the configurations, arrangements, etc. in the above-described embodiments, etc. may be changed as needed, and the above-described embodiments, etc. may be partly combined.

Sixth Embodiment

Figure 18:
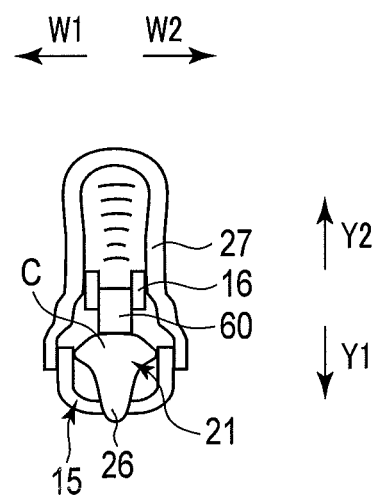
FIG. 18 is a schematic view illustrating a configuration of a first gripper and a second gripper according to a sixth embodiment, in a state in which the first gripper and second gripper are viewed from a distal side.

Next, a sixth embodiment of the present invention will be described with reference to FIG. 18 to FIG. 20. In the meantime, in the sixth embodiment, the configurations of the above-described embodiments, etc. are modified as described below. Incidentally, the same parts as in the above-described embodiments, etc. are denoted by like reference numerals, and a description thereof is omitted. FIG. 18 to FIG. 20 are views illustrating a configuration of a first gripper 26 and a second gripper 27. FIG. 18 illustrating a state as viewed from the distal side (an arrow C1 side in each of FIG. 19 and FIG. 20), and FIG. 19 and FIG. 20 illustrate states as viewed from one side in the width direction of the second gripper 27 (a direction indicated by an arrow W1 and an arrow W2 in FIG. 18). In addition, FIG. 18 and FIG. 19 illustrate a state in which the second gripper 27 is located in the spaced position, and FIG. 20 illustrates a state in which the second gripper 27 is located in the closed position. As illustrated in FIG. 18 to FIG. 20, in the present embodiment, the interlocking actuator (40; 50), which is shown in the above-described embodiments, etc., is not provided. Instead, a pushing portion 60, which is formed of, for example, a cam, is attached as an interlocking actuator, in a state in which the pushing portion 60 is fixed to the second gripper 27.

As illustrated in FIG. 18 and FIG. 19, in the state in which the second gripper 27 is located in the spaced position relative to the first gripper 26, the pushing portion 60 abuts on the first gripper 26, and pushes the first gripper 26 toward a side away from the second gripper 27 (an arrow Y1 side in each of FIG. 18 to FIG. 20). Since the first gripper 26 is pushed by the pushing portion 60, the first gripper 26 deflects toward the side away from the second gripper 27 in the state in which the second gripper 27 is located in the spaced position relative to the first gripper 26. Incidentally, in each of FIG. 18 to FIG. 20, an arrow Y2 side is a side on which the first gripper 26 approaches the second gripper 27.

As illustrated in FIG. 20, if the movable shaft 16 moves to the distal side and the second gripper 27 moves from the spaced position to the closed position, the pushing portion 60 is spaced apart from the first gripper 26 and is no longer in contact with the first gripper 26. Thus, the first gripper 26 is not pushed by the pushing portion 60, and enters a non-deflected state. In addition, the spacing distance between the first gripper 26 and second gripper 27 decreases in accordance with the movement by which the first gripper 26 returns to the non-deflected state in interlock with the movement of the second gripper 27 to the closed position. Accordingly, in the present embodiment, when the first gripper 26 and second gripper 27 are closed with respect to each other by the movement of the movable shaft 16 to the distal side, the spacing distance between the first gripper 26 and second griper 27 decreases due to the movement of the second gripper 27 toward the closed position, and also the spacing distance between the first gripper 26 and second griper 27 decreases due to the movement by which the first gripper 26 returns to the non-deflected state.

On the other hand, if the movable shaft 16 moves to the proximal side, the first gripper 26 is pushed by the pushing portion 60 in interlock with the movement of the second gripper 27 from the closed position to the spaced position, and the first gripper 26 deflects toward the side away from the second gripper 27. The spacing distance between the first gripper 26 and second gripper 27 increases in accordance with the movement by which the first gripper 26 deflects in interlock with the movement of the second gripper 27 to the spaced position. Specifically, the spacing distance between the first gripper 26 and second gripper 27 increases in accordance with the movement of the first gripper 26, which is in interlock with the movement of the second gripper 27 toward the spaced position. Accordingly, in the present embodiment, when the first gripper 26 and second gripper 27 are opened with respect to each other by the movement of the movable shaft 16 to the proximal side, the spacing distance between the first gripper 26 and second griper 27 increases due to the movement of the second gripper 27 toward the spaced position, and also the spacing distance between the first gripper 26 and second griper 27 increases due to the deflecting of the first gripper 26.

In the present embodiment, too, the vibration transmitting member 21 (transmitting member main body 25 and first gripper 26) is formed as one piece. In addition, as described above, also in this embodiment, when the first gripper 26 and second gripper 27 are opened with respect to each other, both the first gripper 26 and the second gripper 27 move to increase the spacing distance from each other. Therefore, in this embodiment, like the above-described embodiments, etc., there can be provided the ultrasonic treatment instrument 1 in which the spacing distance in the state in which the first gripper 26 and second gripper 27 are opened is sufficiently secured and the ultrasonic vibration is properly transmitted to the end effector 10.

Other Modifications

In the above-described embodiments, etc. including the first embodiment to sixth embodiment, the ultrasonic treatment instrument (1) includes the vibration transmitting member (21) which has the longitudinal axis (C), and which includes the first gripper (26) in the distal portion thereof. The vibration transmitting member (21) transmits ultrasonic vibration toward the first gripper (26), and is formed as one piece. In addition, the ultrasonic treatment instrument (1) includes the second gripper (27) which is movable between the spaced position where the second gripper (27) is spaced apart from the first gripper (26) and the closed position where the second gripper (27) is put in close to the first gripper (26). Furthermore, the ultrasonic treatment instrument (1) is provided with the interlocking actuator (40; 50; 60) which increases, by moving the first gripper (26) in interlock with the movement of the second gripper (27) to the spaced position, the spacing distance between the first gripper (26) and second gripper (27) in accordance with the movement of the first gripper (26).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An ultrasonic treatment instrument comprising:
   a one piece vibration transmitting member having a longitudinal axis and a first gripper in a distal portion thereof, and configured to transmit ultrasonic vibration to the first gripper;

a second gripper (1) having a gripping surface and (2) which is movable between an open position in which the gripping surface is spaced from the first gripper and a closed position in which the gripping surface is adjacent to the first gripper;

a tube (1) fixed to and surrounding a portion of the vibration transmitting member, (2) having an outer cylindrical surface, and (3) having a lower vibration transmissibility than the vibration transmitting member, the tube having a groove in the outer cylindrical surface;

a movable cylindrical shaft that encases a part of the tube and the vibration transmitting member;

a handle that moves the movable cylindrical shaft when the handle is operated;

a slider which is attached on an outer surface of the movable cylindrical shaft, and to which the handle is coupled; and an elastic member which extends on the outer surface of the movable cylindrical shaft, and which connects the movable cylindrical shaft and the slider; wherein:

movement of the movable cylindrical shaft causes the second gripper to move between the open position and the closed position; and the movable cylindrical shaft includes an inwardly extending projection that slidably engages the groove in the outer cylindrical surface of the tube to rotate the vibration transmitting member and the tube when the movable cylindrical shaft is moved in synchronization with the movement of the second gripper, such that the first gripper is in a first position when the second gripper is in the open position and the first gripper is in a second position when the second gripper is in the closed position.

2. The ultrasonic treatment instrument of claim 1, wherein the first gripper is curved relative to the longitudinal axis.

3. The ultrasonic treatment instrument of claim 2, wherein:

the movable cylindrical shaft is configured to slide linearly along the longitudinal axis of the vibration transmitting member; and the inwardly extending projection of the movable cylindrical shaft and the groove in the outer cylindrical surface of the tube are configured to convert the linear movement of the movable cylindrical shaft to a rotational movement of the vibration transmitting member and the tube around the longitudinal axis of the vibration transmitting member.

4. The ultrasonic treatment instrument of claim 3, further comprising:

a cylindrical sheath that encases the movable cylindrical shaft and through which the vibration transmitting member is inserted in a state in which the first gripper projects toward a distal side of the cylindrical sheath, the second gripper being rotatably attached to a distal portion of the cylindrical sheath; and a housing having distal and proximal sides, the cylindrical sheath is coupled to the distal side of the housing in a manner to be rotatable relative to the housing around the longitudinal axis of the vibration transmitting member;

wherein:

the tube and the movable cylindrical shaft are configured to rotate around the longitudinal axis of the vibration transmitting member together with the cylindrical sheath;

the groove includes a first groove portion and a second groove portion, the first groove portion and the second groove portion being continuous;

the inwardly extending projection of the movable cylindrical shaft and the groove in the outer cylindrical surface of the tube are configured and located such that when the inwardly extending projection of the movable cylindrical shaft is in the first groove portion of the groove in the outer cylindrical surface of the tube, the second gripper is in the open position; and rotational driving force is transmitted to the tube and the vibration transmitting member by the movement of the inwardly extending projection of the movable cylindrical shaft through the second groove portion.

5. The ultrasonic treatment instrument of claim 4, wherein:

the groove includes a third groove portion continuous with the second groove portion opposite the first groove portion; and when the inwardly extending projection of the movable cylindrical shaft is in the third groove portion, the second gripper is in the closed position.

* * * * *